US010064931B2

(12) United States Patent
Weiner et al.

(10) Patent No.: US 10,064,931 B2
(45) Date of Patent: Sep. 4, 2018

(54) PROTEINS COMPRISING MRSA PBP2A AND FRAGMENTS THEREOF, NUCLEIC ACIDS ENCODING THE SAME, AND COMPOSITIONS AND THEIR USE TO PREVENT AND TREAT MRSA INFECTIONS

(71) Applicant: The Trustees of the University of Pennsylvania, Philadelphia, PA (US)

(72) Inventors: David B. Weiner, Merion, PA (US); Matthew P. Morrow, Bala Cynwyd, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/675,823

(22) Filed: Aug. 14, 2017

(65) Prior Publication Data

US 2018/0028640 A1 Feb. 1, 2018

Related U.S. Application Data

(62) Division of application No. 14/365,071, filed as application No. PCT/US2012/069014 on Dec. 11, 2012, now Pat. No. 9,750,795.

(Continued)

(51) Int. Cl.
*A61K 39/085* (2006.01)
*A61K 38/20* (2006.01)
(Continued)

(52) U.S. Cl.
CPC ............ *A61K 39/085* (2013.01); *A61K 38/20* (2013.01); *A61K 38/208* (2013.01);
(Continued)

(58) Field of Classification Search
CPC ........ C12N 15/57; C12N 15/31; C12N 15/62; C12N 9/52; C07K 3/18
(Continued)

(56) References Cited

U.S. PATENT DOCUMENTS

2002/0123099 A1 9/2002 Weiner
2004/0082002 A1 4/2004 Choi
(Continued)

FOREIGN PATENT DOCUMENTS

CA 2813466 4/2012
EP 0505151 A2 9/1992
(Continued)

OTHER PUBLICATIONS

Lim et al., "Structural basis for the f:l-lactam resistance of PBP2a from methicillin-resistant *Staphylococcus aureus*," 2002, Nature Structural & Molecular Biology, 9(11):870-876.

(Continued)

*Primary Examiner* — Jana A Hines
(74) *Attorney, Agent, or Firm* — Riverside Law LLP

(57) ABSTRACT

Nucleic acid molecules which encode an MRSA PBP2a protein or a fragment thereof which comprises at least 245 amino acid are disclosed. Compositions comprising the nucleic acid molecules are disclosed. Novel proteins which comprise a MRSA PBP2a protein or a fragment thereof which comprises at least 245 amino acid are disclosed are disclosed. Methods of inducing an immune response against MRSA PBP2a are disclosed, as are methods of treating an individual who has been diagnosed with MRSA and methods of preventing MRSA infection in an individual.

18 Claims, 9 Drawing Sheets

Specification includes a Sequence Listing.

Related U.S. Application Data

(60) Provisional application No. 61/569,727, filed on Dec. 12, 2011.

(51) Int. Cl.
*C07K 14/31* (2006.01)
*C12Q 1/689* (2018.01)

(52) U.S. Cl.
CPC .......... *A61K 38/2086* (2013.01); *C07K 14/31* (2013.01); *C12Q 1/689* (2013.01)

(58) Field of Classification Search
USPC ......... 424/93.1, 93.2, 93.4, 93.42; 435/252.1
See application file for complete search history.

(56) References Cited

U.S. PATENT DOCUMENTS

| | | | |
|---|---|---|---|
| 2004/0147734 | A1 | 7/2004 | Doucette-Stamm |
| 2010/0119477 | A1 | 5/2010 | Otto et al. |
| 2010/0166787 | A1 | 7/2010 | Weiner |
| 2010/0291144 | A1 | 11/2010 | Ramanathan et al. |

FOREIGN PATENT DOCUMENTS

| | | | |
|---|---|---|---|
| EP | 0875578 | A2 | 11/1998 |
| WO | 2005000235 | A2 | 1/2005 |
| WO | 2009158284 | A2 | 12/2009 |
| WO | 2010057159 | A2 | 5/2010 |

OTHER PUBLICATIONS

Oliveira et al., "Genetic organization of the downstream region of the mecA element in methicillin-resistant *Staphylococcus aureus* isolates carrying different polymorphisms of this region," 2000, Antimicrobial Agents and chemotherapy, 44:1906-1910-UniProt, Accession No. Q9KJC9.

Dhwada et al., "DNA vaccination by mecA sequence evokes an antibacterial immune response against methicillin-resistant *Staphylococcus aureus*," 1999, The Journal of antimicrobial chemotherapy, 44(6):767-74.

Senna et al., "Protective immune response against methicillin resistant *Staphylococcus aureus* in a murine model using a DNA vaccine approach," 2003, Vaccine, 21(19-20):2661-6.

Roth et al., "Evaluation of the humoral immune response in BALB/c mice immunized with a naked DNA vaccine anti-methicillin-resistant *Staphylococcus aureus*," 2006, Genetics and Molecular Research, 5(3):503-12.

Williams, Amanda J. et al., "Improved Efficacy of a Gene Optimised Adenovirus-based Vaccine for Venezuelan Equine Encephalitis Virus", Virology Journal, 2009. vol. 6:118; pp. 1-8.

Graf, Marcus et al., "Concerted Action of Multiple cis-Acting Sequences Is Required for Rev Dependence of Late Human Immunodeficiency Virus Type 1 Gene Expression", Journal of Virology, 2000. vol. 74(22):10822-10826.

Bio View (2008) vol. 55, pp. 42-43.

English Translation of Official Action from Japanese Patent Office relating to Japanese Patent Application No. 2014-547351, dated May 1, 2017.

Anti-PBP2a IgG endpoint titers

PROTEINS COMPRISING MRSA PBP2A AND FRAGMENTS THEREOF, NUCLEIC ACIDS ENCODING THE SAME, AND COMPOSITIONS AND THEIR USE TO PREVENT AND TREAT MRSA INFECTIONS

CROSS-REFERENCE TO RELATED APPLICATIONS

This application is a divisional application of U.S. application Ser. No. 14/365,071, filed Jun. 12, 2014 which is a United States National Stage filing under 35 USC § 371 of International PCT Application Serial No. PCT/US2012/069014, filed Dec. 11, 2012, which claims priority to U.S. Provisional Application No. 61/569,727, filed Dec. 12, 2011, each of which is incorporated herein by reference in its entirety.

FIELD OF THE INVENTION

The present invention relates to consensus antigenic MRSA PBP2a proteins and fragments thereon and nucleic acid molecules which encode the same; to improved MRSA vaccines that include such proteins and/or nucleic acid molecules; and methods for using the vaccines for inducing immune responses and preventing MRSA infection and/or treating individuals infected with MRSA.

BACKGROUND OF THE INVENTION

Methicillin-Sensitive *Staphylococcus aureus* (MSSA) refers to all of the antibiotic-sensitive strains of *Staphylococcus aureus*. Accordingly, MSSA refers to the common type of *Staphylococcus aureus* (*Staph. aureus*) that causes most *Staph. aureus* infections and that can be treated with penicillin-type antibiotics. By contrast, Methicillin-Resistant *Staphylococcus aureus* (MRSA) refers to a subgroup of *Staph. aureus* that is resistant to a range of penicillin antibiotics, including Methicillin. MRSA first appeared in 1961 soon after the introduction of the antibiotic Methicillin. Both MSSA and MRSA have virulence/pathogenicity factors that allow for adhesion to cell surfaces and immune evasion/killing. Studies conducted comparing the pathogenicity of MRSA and MSSA have resulted in some conflicting data. What is clear, however, is that perhaps the most significant difference between MRSA and MSSA is MRSA's resistance to Methicillin. MRSA's resistance arises from the presence of the penicillin-binding protein 2a (PBP2a) protein on the surface of the bacteria. PBP2a protein is encoded by the mecA gene.

*Staph. aureus* infections, including MRSA (Methicillin Resistant *Staph. aureus*), occur most frequently among persons in hospitals and other healthcare facilities, such as for example nursing homes and dialysis centers. These healthcare-associated *Staph* infections include, among others, surgical wound infections, urinary tract infections, bloodstream infections, and pneumonia. MRSA can cause skin infections that may look like a pimple or boil and can be red, swollen, painful, or have pus or other drainage. More serious infections may cause pneumonia, bloodstream infections, or surgical wound•infections. The most recent estimate of the number of people developing a serious MRSA infection (i.e., invasive) is about 94,360 patients. Approximately 18,650 persons died during a hospital stay as the result of a serious MRSA infection (~20% mortality).

Attempts at developing DNA vaccines against MRSA using plasmids with nucleic acid sequences that encode PBP2a or fragments thereof have bee reported. Ohwada A, et al. DNA vaccination by mecA sequence evokes an antibacterial immune response against methicillin-resistant *Staphylococcus aureus*, J Antimicrob Chemother. 1999 December; 44(6):767-74, describes the intramuscular injection of a DNA plasmid that comprises the PBP2a protein-encoding mecA gene cloned from the N315 MRSA isolate. Roth D M, et al. Evaluation of the humoral immune response in BALB/c mice immunized with a naked DNA vaccine anti-methicillin-resistant *Staphylococcus aureus*, Genet Mol Res. 2006 Aug. 31; 5(3):503-12, and Senna J P, et al. Protective immune response against methicillin resistant *Staphylococcus aureus* in a murine model using a DNA vaccine approach. Vaccine. 2003 Jun. 2; 21(19-20):2661-6 report intramuscular injection was used to deliver a DNA plasmid that comprised only a 249 base pair fragment of the mecA gene cloned from the HSP-03 clinical MRSA isolate.

There remains a need for a vaccine useful to prevent or treat MRSA infections. There remains a need for nucleotide sequences that encode MRSA PBP2a or fragments thereof which can be expressed in high levels when incorporated into a vaccine such that effective immune responses against MRSA *Staph. aureus* that expresses PBP2a. are induced, thereby providing therapeutic effects in infected individuals or long-term protection against MRSA infection.

SUMMARY OF THE INVENTION

Nucleic acid molecules are provided which encode a protein that comprises an MRSA PBP2a protein or a fragment thereof which comprise at least 245 amino acids. In some embodiments the protein comprises a signal peptide linked to the MRSA PBP2a protein or a fragment thereof. In some embodiments, the signal peptide is an IgE signal peptide.

Nucleic acid molecules are provided which comprise a fragment of a nucleic acid sequence that is at least 98% homologous to SEQ ID NO:1 and that encodes a protein at least 98% homologous to SEQ ID NO:2. The fragment encodes an immunogenic fragment of a protein that is 98% homologous to a fragment of SEQ ID NO:2 and comprises at least 245 amino acids, such as for example, an immunogenic fragment of SEQ ID NO:2 having at least 245 amino acids. In some embodiments, the fragment comprises a fragment of SEQ ID NO:1, such as for example, SEQ ID NO:3 or SEQ ID NO:5. Fragments are in some embodiments free of coding sequences that encode an MRSA PBP2a transmembrane domain. Fragments in some embodiments are operably linked to a coding sequence that encodes a signal peptide sequence, such as for example an IgE signal peptide sequence SEQ ID NO:13. Fragments in some embodiments comprising SEQ ID NO:9 or SEQ ID NO:11.

Nucleic acid molecules are provided which comprise a nucleic acid sequence that is at least 98% homologous to SEQ ID NO:1 and that encodes a protein at least 98% homologous to SEQ ID NO:2, such as for example a protein comprising SEQ ID NO:2. In some embodiments, nucleic acid molecules are provided which comprise SEQ ID NO:1, a synthetic coding sequence for MRSA PBP2a protein. Nucleic acid coding sequences in some embodiments are operably linked to a coding sequence that encodes a signal peptide sequence, such as for example an IgE signal peptide sequence SEQ ID NO:13. Nucleic acid molecules in some embodiments comprising SEQ ID NO:7.

The nucleic acid molecules that include nucleic acid sequence that encode an MRSA PBP2a protein or a fragment thereof which comprises at least 245 amino acid as set forth above may be plasmids, nucleic acid molecule is incorporated into a viral particle, or other expression vectors.

Compositions are provided which include plasmids or other nucleic acid molecule formulated for delivery to an individual using electroporation.

Compositions are provided which include nucleic acid sequences that encode one or more proteins selected from the group consisting of: IL-12, IL-15 and IL-28.

Proteins are provided. Proteins which are at least 98% homologous to proteins comprising SEQ ID NO:2 are provided as are proteins which comprise an immunogenic fragment of a protein that is at least 98% homologous to a fragment of SEQ ID NO:2 and that comprises at least 245 amino acids. In some embodiments, protein comprise SEQ ID NO:4 or SEQ ID NO:6.

Methods of inducing an immune response against MRSA PBP2a are provided. Some methods comprise administering nucleic acid molecule which encodes a MRSA PBP2a protein, or a fragment thereof which comprises at least 245 amino acid, to an individual in an amount effective to induce an immune response in the individual. Some methods comprise administering the protein to an individual in an amount effective to induce an immune response in the individual.

Method of treating an individual who has been diagnosed with MRSA are provided. Some methods comprise administering nucleic acid molecules which encode an MRSA PBP2a protein or a fragment thereof which comprises at least 245 amino acid to an individual in a therapeutically amount. Some methods comprise administering a therapeutically effective amount of the protein to an individual.

Method of preventing MRSA infection in an individual are provided. Some methods comprise administering nucleic acid molecules which encode an MRSA PBP2a protein or a fragment thereof which comprises at least 245 amino acid to an individual in a prophylactically amount. Some methods comprise administering a prophylactically effective amount of protein to an individual.

BRIEF DESCRIPTION OF THE DRAWINGS

FIG. 1 also shows a depiction of two versions of the PBP2a protein which are examples of PBP2a protein sequences which are included in the protein encoded by nucleic acid molecules disclosed herein. The version designated "Full" includes the full length PBP2a protein including "Transmembrane Domain", the "N Terminal Extension and the Non-Penicillin Binding Domain" and the "Transpeptidase Domain". The version designated "No Anchor" is a fragment of the full length PBP2a protein including the "N Terminal Extension and the Non-Penicillin Binding Domain" and the "Transpeptidase Domain".

DETAILED DESCRIPTION OF THE PREFERRED EMBODIMENT

Figure 1:
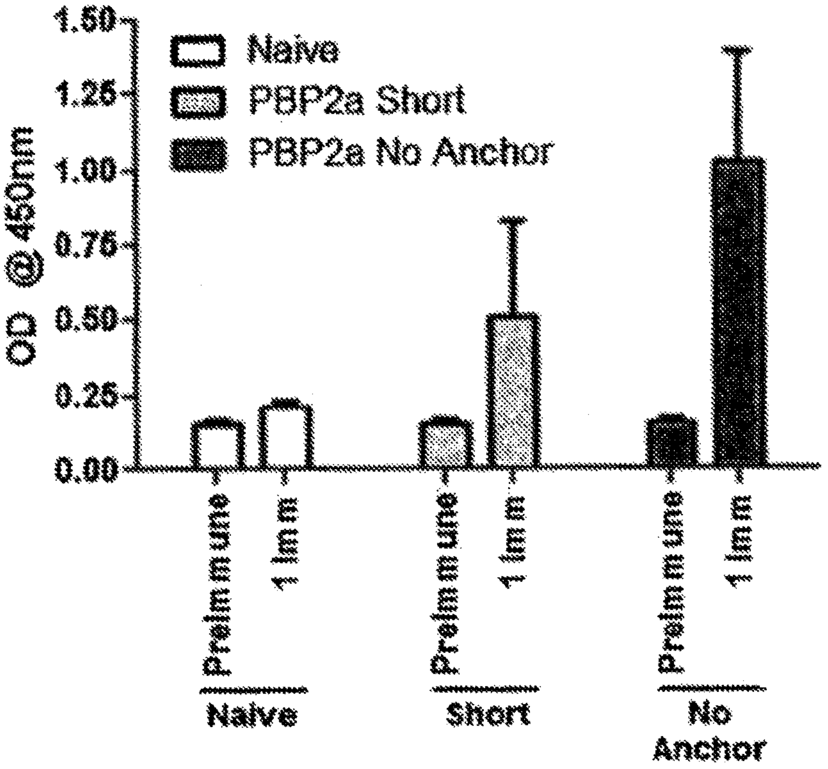
FIG. 1 is an illustration depicting the PBP2a protein as found on the surface of *Staph. aureus*. The protein is anchored in a cell membrane by its "Transmembrane Domain" which is located in the cell membrane and both the "N Terminal Extension and the Non-Penicillin Binding Domain" and the "Transpeptidase Domain" are exposed on the outside of the cell in the extracellular space.

Coding sequences are provided which encode a protein which comprises a consensus MRSA PBP2a or an immunogenic fragment thereof. The coding sequences provide for improved transcription and translation, including having one or more of the following: low GC content leader sequence to increase transcription; mRNA stability and codon optimization; eliminating to the extent possible cis-acting sequence motifs (i.e., internal TATA-boxes). In some embodiments, the coding sequences which encode a protein which comprises a consensus MRSA PBP2a or an immunogenic fragment thereof are operably linked to coding sequences that encode a signal peptide, such as for example the IgE signal peptide. Proteins which comprise a consensus MRSA PBP2a or an immunogenic fragment thereof linked to coding sequences that encode a signal peptide, such as for example the IgE signal peptide are provided. Expression of the coding sequences in cells of an individual or administration of the proteins induce immune responses which recognize MRSA PBP2a protein including MRSA PBP2a protein on the cell surface of *Staph. aureus*.

In some aspects of the invention, the immune responses against MRSA PBP2a provide a broad immune response against multiple strains of bacteria. In some embodiments, proteins comprise full-length MRSA PBP2a sequences and nucleic acid molecules that encode MRSA PBP2a proteins comprise coding sequences that encode full-length MRSA PBP2a sequences. In some embodiments, proteins comprise fragments of MRSA PBP2a sequences and nucleic acid molecules that encode MRSA PBP2a proteins comprise coding sequences that encode fragments of MRSA PBP2a sequences. MRSA PBP2a proteins sequences may be generated from MRSA PBP2a sequences derived from multiple sources, strains, subtypes, subspecies, etc. In some embodiments, the MRSA PBP2a sequence is a computer generated sequences that is a consensus sequence of multiple MRSA PBP2a sequences wherein the consensus sequence utilizes the most commonly occurring amino acid at each position.

In some embodiments, the MRSA PBP2a is provides immune responses with increased cross-reactivity between strains.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance immune responses against MRSA PBP2a encoded by the DNA plasmids and nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to which the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of PBP2a sequences based upon multiple MRSA sequences. The PBP2a sequence disclosed in SEQ ID NO:2 is based upon sequences in Genbank accession numbers CAA74376.1, ADC36253.1, CAH17594.1, CAL22891.1, AAF85645.1, and ABM66443.1. These sequences were aligned and the most common amino acid at each point was selected for use in the finalized antigens. When incorporated into a vaccine, the protein or gene that encodes the protein can be used to induce broad immunity against multiple MRSA PBP2a variants. Consensus MRSA PBP2a may include amino acid sequences and nucleotide sequences that encode such proteins.

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" may mean a polypeptide fragment of PBP2a that is capable of eliciting an immune response in a mammal against PBP2a. A fragment may comprise a fragment of a SEQ ID NO:2. The fragment may comprise SEQ ID NO:6 or other fragments of SEQ ID NO:2, such as SEQ ID NO:4. In some embodiments, the fragment comprises SEQ ID NO:6. In some embodiments, the fragment comprises SEQ ID NO:4. SEQ ID NO:12 comprises SEQ ID NO:6. SEQ ID NO:10 comprises SEQ ID NO:4. Fragments also refer to fragments of a polypeptide that is 98% or more homologous to SEQ ID NO:2. Fragments also refer to fragments of a polypeptide that is 99% or more homologous to SEQ ID NO:2. The fragment may comprise a fragment of a polypeptide that is 98% or more homologous to SEQ ID NO:6 or other fragments of a polypeptide that is 98% or more homologous to SEQ ID NO:2, such as a fragment of a polypeptide that 98% or more homologous to SEQ ID NO:4. In some embodiments, the fragment comprises a fragment of a polypeptide that 98% or more homologous to SEQ ID NO:6. In some embodiments, the fragment comprises a fragment of a polypeptide that 98% or more homologous to SEQ ID NO:4. The fragment may comprise a fragment of a polypeptide that is 99% or more homologous to SEQ ID NO:6 or other fragments of a polypeptide that is 99% or more homologous to SEQ ID NO:2, such as a fragment of a polypeptide that 99% or more homologous to SEQ ID NO:4. In some embodiments, the fragment comprises a fragment of a polypeptide that 99% or more homologous to SEQ ID NO:6. In some embodiments, the fragment comprises a fragment of a polypeptide that 99% or more homologous to SEQ ID NO:4.

The fragments thereof may be 245 or more amino acids in length, 250 or more, 260 or more, 275 or more, 290 or more, 320 or more, 350 or more, 380 or more, 410 or more, 440 or more, 470 or more, 500 or more, 540 or more, 560 or more, 580 or more, 640 or more in length or 660 or more in length Polypeptide fragments may be fewer than 250 amino acids, fewer than 255, fewer than 267, fewer than 283, fewer than 305, fewer than 335, fewer than 365, fewer than 395, fewer than 435, fewer than 455, fewer than 485, fewer than 520, fewer than 550, fewer than 570, fewer than 600, fewer than 650, or fewer than 665 amino acids in length. Fragments preferably do not include the transmembrane domain. Fragments preferably include all or part of the catalytic or transpeptidase domain which corresponds to the C terminal portion of the molecule. Fragments preferably include all or part of the N terminal extension and non-penicillin binding domain/dimer region. Fragments preferably include all or part of the catalytic or transpeptidase domain which corresponds to the C terminal portion of the molecule and additionally all or part of the N terminal extension and non-penicillin binding domain/dimer region.

Fragments may further comprise a signal peptide such as an immunoglobulin signal peptide, for example an IgE or IgG signal peptide. The signal peptide may be linked to the 667 amino acid PBP2a sequence (668 amino acids minus the N terminal Met) or smaller fragment thereof. The signal peptide may be linked to a polypeptide that is 98% homologous to the 667 amino acid PBP2a sequence (668 amino acids minus the N terminal Met) or to a smaller fragment of a polypeptide that is 98% homologous to the 667 amino acid PBP2a sequence. The signal peptide may be linked to a polypeptide that is 99% homologous to the 667 amino acid PBP2a sequence (668 amino acids minus the N terminal Met) or to a smaller fragment of a polypeptide that is 99% homologous to the 667 amino acid PBP2a sequence. In calculating degrees of homology a polypeptide has to SEQ ID NO:2 or a fragment thereof, any signal peptide is not included in such calculation. The sequences of the signal peptide are not used in determining homology. Thus, for example, although SEQ ID NO:12 comprises SEQ ID NO:6 operably linked to a signal peptide, SEQ ID NO:12 comprises a fragment of SEQ ID NO:2, i.e. SEQ ID NO:12 comprises a polypeptide that is 100% homologous to a fragment of SEQ ID NO:2, notwithstanding the signal peptide which is absent in SEQ ID NO:6. Thus, proteins which comprise fragments of a polypeptide that is at least 98% homologous to a fragment of SEQ ID NO:2 intended to refer to proteins which fragments of a polypeptide that is at least 98% homologous to a fragment of SEQ ID NO:2 that are at least 245 amino acids and may optionally be linked to a, for example, a signal peptide.

"Fragment" may also mean a nucleic acid fragment of that encodes a PBP2a fragment set forth above including nucleic acid fragment of that encodes fragments of SEQ ID NO:2 and fragments of polypeptides that are 98% or more homologous to SEQ ID NO:2. A fragment may mean a nucleic acid fragment of that encodes a protein comprising a fragment of a SEQ ID NO:2. The fragment may mean a nucleic acid fragment of that encodes a protein comprising a fragment of a SEQ ID NO:2 that comprises SEQ ID NO:6 or other fragments of SEQ ID NO:2, such as SEQ ID NO:4. In some embodiments, the fragment is a nucleic acid fragment that encodes a protein comprising SEQ ID NO:6, such as SEQ ID NO:12. In some embodiments, the fragment is a nucleic acid fragment of that encodes a protein comprising SEQ ID NO:4 such as SEQ ID NO:10. "Fragments also refer to nucleic acid fragment that encode a fragment of a polypeptide that is 98% or more homologous to SEQ ID NO:2. Fragments also refer to nucleic acid fragment that encode of fragments of a polypeptide that is 99% or more homologous to SEQ ID NO:2. The fragment may comprise a nucleic acid fragment that encode of a fragment of a polypeptide that is 98% or more homologous to SEQ ID NO:6 or other fragments of a polypeptide that is 98% or more homologous to SEQ ID NO:2, such as a fragment of a polypeptide that 98% or more homologous to SEQ ID NO:4. In some embodiments, the fragment comprises a nucleic acid fragment that encodes of a fragment of a polypeptide that 98% or more homologous to SEQ ID NO:6. In some embodiments, the fragment comprises a nucleic acid fragment that encodes a fragment of a polypeptide that 98% or more homologous to SEQ ID NO:4. The fragment may comprise a nucleic acid fragment that encodes a fragment of a polypeptide that is 99% or more homologous to SEQ ID NO:6 or other fragments of a polypeptide that is 99% or more homologous to SEQ ID NO:2, such as a fragment of a polypeptide that 99% or more homologous to SEQ ID NO:4. In some embodiments, the fragment comprises a nucleic acid fragment that encodes a fragment of a polypeptide that 99% or more homologous to SEQ ID NO:6. In some embodiments, the fragment comprises a nucleic acid fragment that encode of a fragment of a polypeptide that 99% or more homologous to SEQ ID NO:4. "Fragment" as used herein may mean a portion or a nucleic acid that encodes a polypeptide capable of eliciting an anti-PBP2a immune response in a mammal.

Nucleic acid fragments of that encodes a PBP2a fragment set forth above including nucleic acid fragment of that encodes fragments of SEQ ID NO:2 and fragments of polypeptides that are 98% or more homologous to SEQ ID NO:2 are 98% or more homologous to fragments of SEQ ID NO:1. Nucleic acid fragments are preferably 99% or more homologous to fragments of SEQ ID NO:1. Nucleic acid fragments are preferably fragments of SEQ ID NO:1. Nucleic acid molecule fragments thus are 98% or more homologous to fragments of SEQ ID NO:1 and encode proteins that are 98% or more homologous to fragments of SEQ ID NO:2. Nucleic acid molecule fragments thus are preferably 99% or more homologous to fragments of SEQ ID NO:1. Nucleic acid molecule fragments preferably encode proteins that are 99% or more homologous to fragments of SEQ ID NO:2. Nucleic acid molecule fragments thus are 99% or more homologous to fragments of SEQ ID NO:1 and encode proteins that are 99% or more homologous to fragments of SEQ ID NO:2. Nucleic acid molecule fragments preferably encode proteins that are 99% or more homologous to fragments of SEQ ID NO:2. Nucleic acid molecule fragments preferably encode fragments of SEQ ID NO:2. Nucleic acid molecule fragments preferably encode fragments of SEQ ID NO:2 that comprise SEQ ID NO:6. Nucleic acid molecule fragments may encode fragments of SEQ ID NO:2 that comprise SEQ ID NO:6. Nucleic acid molecule fragments may encode fragments of SEQ ID NO:2 that comprise SEQ ID NO:4. Nucleic acid molecule fragments may comprise SEQ ID NO:5. Nucleic acid molecule may comprise SEQ ID NO:3.

Nucleic acid molecule fragments encode fragments of PBP2a that are 245 or more amino acids in length, 250 or more, 260 or more, 275 or more, 290 or more, 320 or more, 350 or more, 380 or more, 410 or more, 440 or more, 470 or more, 500 or more, 540 or more, 560 or more, 580 or more, 640 or more in length or 660 or more in length. The fragments thereof may comprise SEQ ID NO:5 such as SEQ ID NO: 9. The fragments thereof may comprise SEQ ID NO:7 such as SEQ ID NO:11. Fragments of SEQ ID NO:1 or of a nucleotide sequence at least 98% homologous to a fragment SEQ ID NO:1 that encodes a fragment of SEQ ID NO:2 or a fragment of a polypeptide that is at least 98% homologous to a fragment SEQ ID NO:2 may encode fragments of PBP2a that are 245 or more amino acids in length, 250 or more, 260 or more, 275 or more, 290 or more, 320 or more, 350 or more, 380 or more, 410 or more, 440 or more, 470 or more, 500 or more, 540 or more, 560 or more, 580 or more, 640 or more in length or 660 or more in length. Fragments of SEQ ID NO:1 or of a nucleotide sequence at least 98% homologous to a fragment SEQ ID NO:1 that encodes a fragment of SEQ ID NO:2 or a fragment of a polypeptide that is at least 98% homologous to a fragment SEQ ID NO:2 are fewer than 250 amino acids, fewer than 255, fewer than 267, fewer than 283, fewer than 305, fewer than 335, fewer than 365, fewer than 395, fewer than 435, fewer than 455, fewer than 485, fewer than 520, fewer than 550, fewer than 570, fewer than 600, fewer than 650, or fewer than 665 amino acids in length. Fragments of SEQ ID NO:1 or of a nucleotide sequence at least 98% homologous to a fragment SEQ ID NO:1 that encodes a fragment of SEQ ID NO:2 or a fragment of a polypeptide that is at least 98% homologous to a fragment SEQ ID NO:2 may be 735 or more nucleotides in length, 750 or more, 780 or more, 825 or more, 870 or more, 960 or more, 1050 or more, 1140 or more, 1230 or more, 1320 or more, 1410 or more, 1500 or more, 1620 or more, 1680 or more, 1740 or more, 1920 or more in length or 1980 or more in length. Fragments of SEQ ID NO:1 or of a nucleotide sequence at least 98% homologous to a fragment SEQ ID NO:1 that encodes a fragment of SEQ ID NO:2 or a fragment of a polypeptide that is at least 98% homologous to a fragment SEQ ID NO:2 may be fewer than 750 nucleotides in length, fewer than 765, fewer than 800, fewer than 850, fewer than 915, fewer than 1000, fewer than 1100, fewer than 1200, fewer than 1300, fewer than 1350, fewer than 1550, fewer than 1600, fewer than 1650, fewer than 1700, fewer than 1800, fewer than 1950, or fewer than 1995 nucleotides in length. Fragments preferably do not encode the transmembrane domain. Fragments preferably encode all or part of the catalytic or transpeptidase domain which corresponds to the C terminal portion of the protein. Fragments preferably encode all or part of the catalytic or transpeptidase domain which corresponds to the C terminal portion of the protein and additionally all or part of the N terminal extension and non-penicillin binding domain/dimer region.

DNA fragments may comprise coding sequences that encode a signal peptide such as an immunoglobulin signal peptide, for example an IgE or IgG signal peptide. Coding sequences that encode the signal peptide may be linked coding sequences that encode the 667 amino acid PBP2a sequence (668 amino acids minus the N terminal Met) or smaller fragment thereof. The coding sequences that encode signal peptide may be linked to coding sequences that encode a polypeptide that is at least 98% homologous to the 667 amino acid PBP2a sequence (668 amino acids minus the N terminal Met) or to a smaller fragment of a polypeptide that is at least 98% homologous to the 667 amino acid PBP2a sequence. The coding sequences that encode the signal peptide may be linked to coding sequences that encode a polypeptide that is at least 99% homologous to the 667 amino acid PBP2a sequence (668 amino acids minus the N terminal Met) or to a smaller fragment of a polypeptide that is at least 99% homologous to the 667 amino acid PBP2a sequence. The coding sequences are at least 98% homologous to a fragment of SEQ ID NO:1, preferably at least 99% or more homologous to a fragment of SEQ ID NO:1. The coding sequences are preferably 100% homologous to a fragment of SEQ ID NO:1, i.e. they are a fragment of SEQ ID NO:1. As noted above in describing the calculation of degrees of homology to SEQ ID NO:2 or a fragment thereof for peptide sequence, calculation of degrees of homology for coding sequences do not include coding sequences that encode signal peptides in such calculation. The sequences of the signal peptide are not used in determining degree of homology between coding sequences and fragments of SEQ ID NO:1. Thus, for example, although SEQ ID NO:11 comprises SEQ ID NO:5 operably linked to a signal peptide, SEQ ID NO:11 comprises a fragment of SEQ ID NO:1, i.e. SEQ ID NO:11 comprises a nucleotide sequence that is 100% homologous to a fragment of SEQ ID NO:1, notwithstanding the fact that the coding sequence in SEQ ID NO:11 that encodes the signal peptide is not included in SEQ ID NO:1. Thus, nucleic acid molecules which comprise fragments of a nucleic acid sequence that is at least 98% homologous to a fragment of SEQ ID NO:1 intended to refer to nucleic acid molecules which comprise fragments of a nucleic acid sequence that is at least 98% homologous to a fragment of SEQ ID NO:1 and encodes at least 245 amino acids at least 98% homologous to a fragment of SEQ ID NO:2 and may optionally be linked to a, for example, coding sequence of a signal peptide.

l. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

m. Impedance

"Impedance" as used herein may be used when discussing the feedback mechanism and can be converted to a current value according to Ohm's law, thus enabling comparisons with the preset current.

n. Immune Response

"Immune response" as used herein may mean the activation of a host's immune system, e.g., that of a mammal, in response to the introduction of the MRSA PBP2a protein via the provided DNA plasmid vaccines. The immune response can be in the form of a cellular or humoral response, or both.

o. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

p. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

q. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

r. Signal Peptide

"Signal peptide" refers to a short peptide sequence, typically less than 50 amino acids long, which directs the transport of the protein in which it is incorporated. Signal peptides typically are linked to a protein at the N terminus and coding sequences encoding the signal peptide often include the initiation codon that encodes the N terminal methionine encoded by the initiation codon. Signal peptides target the protein for transport within the cell and are involved in the secretory pathway in which the presence of the signal peptide on a protein targets the protein for transport though the secretory pathway such that the protein is secreted by the cell or otherwise targeted for release by the cell into the extracellular environment. In some embodiments, the signal peptide is an immunoglobulin signal peptide such as an IgG or IgE signal peptide. The addition of a coding sequence of a signal peptide to the coding sequences of a protein generally refers to the insertion of the coding sequence of a signal peptide including an initiation codon in place of the initiation codon of the coding sequence of the protein. That is, the addition of the coding sequence of a signal peptide to the coding sequence of the protein involves the removal of the initiation codon of the coding sequence of the protein and the insertion of the coding sequence of a signal peptide including an initiation codon. Thus, in the single peptide plus protein encoded thereby, the methionine at position 1 of the amino acid sequence of the original protein sequence is replaced by the amino acid sequence of the signal peptide which has a methionine at position 1.

s. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

u. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

v. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

w. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. PBP2a Protein

Several amino acid sequences PBP2a protein are disclosed in Genbank such as for example those having accession numbers NP_370565.1, ZP_06791480.1, BAG06200.1, AAX14397.1, YP_184944.1, BAK53145.1, ADC53332.1, BAE75884.1, ZP_07362739.1, ADC53314.1, CAL22891.1, CBI47957.1, CAH17594.1, CAA74376.1, ADC36253.1, ADV68980.1, ADV68968.1, AAF85645.1, and ABM66443.1. MRSA PBP2a protein. The variously reported sequences have slight variations but the length of the protein is generally 667 amino acids although some differences do exist among different strains and isolates. As used herein, for convenience the PBP2a protein is referred to as a 668 amino acid protein including the N terminal methionine encoded by the start codon. The numbering of the different domains set forth herein refer to the amino acid sequence SEQ ID NO:2 which is a full length PBP2a sequence referred to above as a consensus sequence based upon sequences in Genbank accession numbers CAA74376.1, ADC36253.1, CAH17594.1, CAL22891.1, AAF85645.1, and ABM66443.1.

The full length PBP2a protein is a cell surface protein has three domains which are depicted in FIG. 1. The left side of FIG. 1 shows the depiction of the PBP2a protein anchored in a cell membrane with the "Transmembrane Domain" within the cell membrane and both the "N Terminal Extension and the Non-Penicillin Binding Domain" and the "Transpeptidase Domain" exposed on the outside of the cell in the extracellular space. The right side of FIG. 1 shows a depiction of the "Full" and "No Anchor" versions of the protein encoded by the constructs herein. The "Full" includes "Transmembrane Domain", the "N Terminal Extension and the Non-Penicillin Binding Domain" and the "Transpeptidase Domain" while the "No Anchor" includes the "N Terminal Extension and the Non-Penicillin Binding Domain" and the "Transpeptidase Domain". The transmembrane domain which is at the N terminus of the protein and anchors the protein at the cell membrane corresponds to amino acids 1-23. Amino acids 27-326 are referred to as the non-penicillin binding domain and include amino acids 27-138 which are referred to as the N terminal extension. Amino acids 327-668 are referred as the transpeptidase or catalytic domain. Amino acids 24-140 are also referred to as the MecA_N region or "NTF2-like N-terminal transpeptidase domain". Amino acids 136-667 are also referred to as the FtsI region and include amino acids 147-310 which is also referred to as the PBP Dimer region or "Penicillin-binding Protein dimerisation domain" and amino acids 345-658 which is also referred to as the Transpeptidase region or "Transpeptidase domain".

Provided herein is a consensus MRSA PBP2a protein capable of eliciting an immune response in a mammal against MRSA PBP2a. In some embodiments, the MRSA PBP2a protein may be one or more proteins selected from the group consisting of: MRSA PBP2a full length (SEQ ID NO:2), or fragments of MRSA PBP2a full length sequence set forth in SEQ ID NO:2 that comprise at least 245 amino acids. Additionally, the MRSA PBP2a protein may be 98% homologous to SEQ ID NO:2 or it may be a fragment of a protein that is 98% homologous to a fragment of SEQ ID NO:2. SEQ ID NO:2 discloses 667 of the 668 consensus sequence. The N terminal methionine encoded by the initiation codon is not shown in SEQ ID NO:2. However, if some embodiments, it is contemplated that no signal peptide would be included. Thus the coding sequence in SEQ ID NO:1 would be provided with an initiation codon and the polypeptide sequence would thereby comprise SEQ ID NO:2 with an N terminal methionine. Thus for the purposes of this disclosure, it is intended that a nucleic acid molecule comprising SEQ ID NO:1 with an initiation codon (ATG) is disclosed, as is intended a polypeptide comprising SEQ ID NO:2 with an N terminal methionine. Fragments and homologous variant thereof are also intended to be described herein having an initiation codon (ATG) and N terminal methionine in nucleotide sequences and amino acid sequences. Thus for example, fragments of SEQ ID NO:1, such as SEQ ID NO:3 and SEQ ID NO:5, or fragments of nucleic acid sequences at least 98% homologous to SEQ ID NO:1 are intended to be disclosed as further comprising an initiation codon (ATG). Likewise, fragments of SEQ ID NO:2, such as SEQ ID NO:4 and SEQ ID NO:6, or fragments of at least 8% homologous SEQ ID NO:2 are intended to be disclosed as further comprising an N terminal methionine. Likewise, fragments of SEQ ID NO:2, such as SEQ ID NO:4 and SEQ ID NO:6, or fragments of at least 98% homologous SEQ ID NO:2 are intended to be disclosed as further comprising an N terminal methionine.

In some embodiments, the antigen may comprise a peptide a signal peptide sequence. In some embodiments, the antigen may comprise an IgE signal peptide sequence as set forth in SEQ ID NO:13. In some embodiments, the antigen may comprise "Full" SEQ ID NO:8, which is made up of a MRSA PBP2a full length (SEQ ID NO. 2) that has linked at its N terminus the IgE signal peptide sequence (SEQ ID NO:13).

Fragments of MRSA PBP2a full length sequence set forth in SEQ ID NO:2 comprise at least 245 amino acids. In some embodiments, fragments set forth herein may comprise a signal peptide sequence. In some embodiments, the fragments set forth herein may comprise an IgE signal peptide sequence as set forth in SEQ ID NO:13. In some embodiments, the antigen may comprise "No Anchor" SEQ ID NO:10, which is made up of a fragment of MRSA PBP2a having SEQ ID NO. 4 that has linked at its N terminus the IgE signal peptide sequence (SEQ ID NO:13). In some embodiments, the antigen may comprise "Short" SEQ ID NO:12, which is made up of a fragment of MRSA PBP2a having SEQ ID NO:6 that has linked at its N terminus the IgE signal peptide sequence (SEQ ID NO:13).

In some embodiments, fragments do not include the MRSA PBP2a transmembrane domain (amino acids 1-23). In some embodiments, fragments include all or some of the MRSA PBP2a Transpeptidase domain (amino acids 327-668) or at least 245 amino acid sequences from this region. In some embodiments, fragments include all or some of the MRSA PBP2a Transpeptidase domain including amino acids 345-658 or at least 245 amino acid sequences from this region. In some embodiments, fragments include at least 245 amino acid sequences of the most C terminus region of the full length sequence. In some embodiments, fragments include at least 245 amino acid sequences of the 275 most C terminus region (amino acids 393-668) of the full length sequence (i.e. spanning from amino acids 393-638 to amino acids 423-668 and all fragments there between). In some embodiments, fragments include all or some of the MRSA PBP2a Transpeptidase domain (amino acids 327-668) or at least 300 amino acid sequences from this region. In some embodiments, fragments include all or some of the MRSA PBP2a Transpeptidase domain including amino acids 345-658 or at least 300 amino acid sequences from this region. In some embodiments, fragments include at least 340 amino acid sequences of the most C terminus region of the full length sequence. In some embodiments, fragments include at least 340 amino acid sequences of the 400 most C terminus region (amino acids 268-668) of the full length sequence (i.e. spanning from amino acids 268-608 to amino acids 328-668 and all fragments there between). In some embodiments, fragments set forth herein may comprise a signal peptide sequence. In some embodiments, the fragments set forth herein may comprise an IgE signal peptide sequence as set forth in SEQ ID NO:13.

In some embodiments, fragments include all or some of the MRSA PBP2a Transpeptidase domain (amino acids 327-668) and all or some of the non-penicillin binding domain (amino acids 27-326). In some embodiments, fragments include at least 400 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments include at least 450 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments include at least 500 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments include at least 550 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments include at least 600 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments include at least 640 amino acid sequences including all or some of the MRSA PBP2a Transpeptidase domain and all or some of the non-penicillin binding domain including amino acids, and in some embodiments additionally free of the transmembrane domain (most or all of amino acids 1-23). In some embodiments, fragments set forth herein may comprise a signal peptide sequence. In some embodiments, the fragments set forth herein may comprise an IgE signal peptide sequence as set forth in SEQ ID NO:13.

Fragments preferably include much or all of the Transpeptidase domain. Fragments of SEQ ID NO:2 comprising 400 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 425 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 450 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 475 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 500 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 525 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 550 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 575 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 600 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. Fragments of SEQ ID NO:2 comprising 630 or more amino acids preferably comprise at one of more of amino acids 638, 639, 640, 641, 642, 643, 644, 645, 646, 647, 648, 649, 650, 651, 652, 653, 654, 655, 656, 657, 658, 659, 660, 661, 662, 663, 664, 665, 666, 667 or 668 from the PBP2a C terminus. In some embodiments, fragments set forth herein may comprise a signal peptide sequence. In some embodiments, the fragments set forth herein may comprise an IgE signal peptide sequence as set forth in SEQ ID NO:13.

In some embodiments, the fragment may be MRSA PBP2a no anchor/no transmembrane domain) (SEQ ID NO. 4). In some embodiments, the fragment may be "No Anchor" (SEQ ID NO. 10) which is MRSA PBP2a no anchor/no transmembrane domain (SEQ ID NO. 4) plus IgE signal peptide (SEQ ID NO. 13). In some embodiments, the fragment may be or PBP2a "Short" (SEQ ID NO:12) which is MRSA PBP2a short/catalytic domain only, (i.e. catalytic domain only) (SEQ ID NO:6) plus IgE signal peptide (SEQ ID NO. 13).

In addition to SEQ ID NO. 2, a MRSA PBP2a protein may have an amino acid sequence with 98% homology to SEQ ID:NO:2 and fragments of MRSA PBP2a protein include the fragments such as those disclosed herein and corresponding fragments of the a MRSA PBP2a protein that has an amino acid sequence with 98% homology to SEQ ID:NO:2. The MRSA PBP2a protein may has an amino acid sequence with 98% homology to SEQ ID:NO:2 may also additionally comprise a signal peptide sequence, such as for example an IgE signal peptide sequence as set forth in SEQ ID NO:13, although the signal peptide is not included in homology determinations. Likewise, fragments disclosed herein including fragments of the MRSA PBP2a protein that has an amino acid sequence with 98% homology to SEQ ID:NO:2 may further comprise a signal peptide sequence, such as for example an IgE signal peptide sequence as set forth in SEQ ID NO:13, although the signal peptide is not included in homology determinations.

3. PBP2a Coding Sequences

Genbank contains sequences for complete genome of *Staph. aureus* isolates. Several nucleotide sequences of the mecA coding sequence are disclosed in Genbank such as for example those having accession numbers FR823294.1, EF190335.1, AB221121.1, AB221122.1, AB221124.1, AB221120.1, AB221119.1, E09771.1, AB236888.1, AB221123.1, AB063481.1 and X52593.1.

Provided herein are coding sequences that encode MRSA PBP2a proteins capable of eliciting an immune response in a mammal against MRSA PBP2a. In some embodiments, the coding sequence encode an MRSA PBP2a protein selected from the group consisting of: MRSA PBP2a full length (SEQ ID NO:2), or fragments of MRSA PBP2a full length sequence set forth in SEQ ID NO:2 that comprise at least 245 amino acids. Additionally, the coding sequence may encode a MRSA PBP2a protein that is at least 98% homologous to SEQ ID NO:2 or a fragment of a protein that is 98% homologous to a fragment of SEQ ID NO:2.

In some embodiments, the coding sequence is selected from the group consisting of: SEQ ID NO:1, fragments of SEQ ID NO:2 that encode at least 245 amino acids, coding sequences that are at least 98% homologous to SEQ ID NO:1 and encode a protein that is at least 98% homologous to SEQ ID NO:2, and fragments of a coding sequences that is at least 98% homologous to SEQ ID NO:1 and encodes a protein that is at least 98% homologous to SEQ ID NO:2, such fragment comprising at least 245 amino acids.

In some embodiments, the coding sequence further comprises coding sequence for a signal peptide sequence operably linked to the MRSA PBP2a coding sequence. In some embodiments, the coding sequence for a signal peptide sequence encodes an IgE signal peptide sequence as set forth in SEQ ID NO:13. In some embodiments, the coding sequence may comprise SEQ ID NO:7 ("Full") which is made up of coding sequence SEQ ID NO:1 of the MRSA PBP2a full length (SEQ ID NO. 2) linked to coding sequence for the IgE signal peptide sequence (SEQ ID NO:13) such that when expressed, the IgE signal peptide is at the N terminus of the protein.

In some embodiments, the coding sequence comprises a fragment of a nucleic acid sequence that is at least 98% homologous to SEQ ID NO:1 and that encodes a protein at least 98% homologous to SEQ ID NO:2. In some embodiments, the coding sequence comprises a fragment of a nucleic acid sequence that is at least 98% homologous to SEQ ID NO:1 and that encodes a fragment of SEQ ID NO:2 that is at least 245 amino acids. In some embodiments, the coding sequence comprises a fragment of SEQ ID NO:1 that encodes at least 245 amino acids. In some embodiments, the coding sequence comprises a fragment of SEQ ID NO:1 that encodes at least 245 amino acids operably linked to coding sequence for a signal peptide sequence, preferably the IgE signal peptide (SEQ ID NO:13). In some embodiments, the coding sequence comprises SEQ ID NO:3. In some embodiments, the coding sequence comprises SEQ ID NO:3 and further comprises operably linked coding sequence that encodes a signal peptide sequence, preferably the IgE signal peptide. In some embodiments, the coding sequence comprises SEQ ID NO:9. In some embodiments, the coding sequence comprises SEQ ID NO:5. In some embodiments, the coding sequence comprises SEQ ID NO:5 and further comprises operably linked coding sequence that encodes a signal peptide sequence, preferably the IgE signal peptide. In some embodiments, the coding sequence comprises SEQ ID NO:11.

In some embodiments, coding sequences that comprise a fragment of a nucleic acid sequence that is at least 98% homologous to SEQ ID NO:1 that encode immunogenic fragment of a protein that is 98% homologous to a fragment of SEQ ID NO:2 do not encode the MRSA PBP2a transmembrane domain. In some embodiments, coding sequences that comprise a fragment of a nucleic acid sequence that is at least 98% homologous to SEQ ID NO:1 that encode immunogenic fragment of SEQ ID NO:2 do not encode the MRSA PBP2a transmembrane domain. In some embodiments, coding sequences that comprise a fragment of SEQ ID NO:1 do not encode the MRSA PBP2a transmembrane domain. Such coding sequences preferably include coding sequence for a signal peptide sequence, preferably the IgE signal peptide.

In some embodiments, coding sequences encode fragments set forth in the above section enumerated as section 2 and entitled "PBP2a Protein". In some embodiments, coding sequences that encode fragments set forth in the above section enumerated as section 2 and entitled "PBP2a Protein" are fragments of SEQ ID NO:1 and may preferably further include coding sequence for a signal peptide sequence, preferably the IgE signal peptide. In some embodiments, coding sequences that encode fragments set forth in the above section enumerated as section 2 and entitled "PBP2a Protein" are fragments of a coding sequence that is 98% homologous to SEQ ID NO:1 and may preferably further include coding sequence for a signal peptide sequence, preferably the IgE signal peptide. In some embodiments, coding sequences that encode fragments set forth in the above section enumerated as section 2 and entitled "PBP2a Protein" are fragments of a coding sequence that is 98% homologous to SEQ ID NO:1 and encode immunogenic fragments of SEQ ID NO:2, and may preferably further include coding sequence for a signal peptide sequence, preferably the IgE signal peptide.

4. Plasmid

Provided herein is a vector that is capable of expressing MRSA PBP2a protein or a fragment thereof in the cell of a mammal in a quantity effective to elicit an immune response in the mammal. The vector may comprise heterologous nucleic acid encoding the MRSA PBP2a protein or a fragment thereof. The vector may be a plasmid. The plasmid may be useful for transfecting cells with nucleic acid encoding the MRSA PBP2a protein or a fragment thereof, which the transformed host cell is cultured and maintained under conditions wherein expression of the MRSA PBP2a protein or a fragment thereof takes place.

The plasmid may comprise a nucleic acid encoding a protein that comprises the MRSA PBP2a protein or a fragment thereof linked to an Ig signal peptide sequence at its N terminus. The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig signal peptide sequence. The coding sequence of the signal peptide sequence may be 5' of the coding sequence. The consensus antigens encoded by this sequence may comprise an N-terminal Ig signal peptide followed by a consensus antigen protein. The N-terminal Ig signal peptide may be IgE or IgG. U.S. Pat. No. 6,733,994, which is incorporated herein by reference, discloses constructs which comprise optimized RNA sequences and IgE signal peptide sequence. PCT application no. PCT/US04/18962 and corresponding U.S. application Ser. No. 10/560,650, which are both incorporated herein by reference, also disclose constructs which comprise IgE signal peptide sequences.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which maybe used for protein production in mammalian cells such as Chinese hamster ovary (CHO) cells.

5. Vaccine

Provided herein is a vaccine capable of generating in a mammal an immune response against MRSA PBP2a. The vaccine may comprise plasmids as discussed above. The vaccine may comprise a plurality of the plasmids, or combinations thereof. The vaccine may be provided to induce a therapeutic or prophylactic immune response against MRSA.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof. In some embodiments adjuvant may be one or more proteins and/or nucleic acid molecules that encode proteins selected from the group consisting of: IL-12, IL-15, IL-28, CTACK, TECK, MEC or RANTES. Examples of IL-12 constructs and sequences are disclosed in PCT Application Serial No. PCT/US1997/019502 and corresponding U.S. application Ser. No. 08/956,865, U.S. Provisional Application Ser. No. 61/569,600, filed Dec. 12, 2011, and entitled "COMPOSITIONS, COMPRISING IMPROVED IL-12 GENETIC CONSTRUCTS AND VACCINES, IMMUNOTHERAPEUTICS AND METHODS OF USING THE SAME", as well as the PCT Application claiming priority to U.S. Provisional Application Ser. No. 61/569,600, filed on the same day as the application filed herewith, each of which is incorporated by reference in its entirety. Examples of IL-15 constructs and sequences are disclosed in PCT Application Serial No. PCT/US04/18962 and corresponding U.S. application Ser. No. 10/560,650, and in PCT Application Serial No. PCT/US07/00886 and corresponding U.S. application Ser. No. 12/160,766, and in PCT application no. PCT/US10/048827, which are each incorporated herein by reference in their entireties. Examples of IL-28 constructs and sequences are disclosed in PCT application no. PCT/US09/039648 and corresponding U.S. application Ser. No. 12/936,192, which are each incorporated herein by reference in its entirety. Examples of RANTES and other constructs and sequences are disclosed in PCT Application Serial No. PCT/US1999/004332 and corresponding U.S. application Ser. No. 09/622,452, which are each incorporated herein by reference in their entireties. Other examples of RANTES constructs and sequences are disclosed in PCT Application Serial No. PCT/US11/024098, which is incorporated herein by reference in its entirety. Examples of RANTES and other constructs and sequences are disclosed in PCT Application Serial No. PCT/US1999/004332 and corresponding U.S. application Ser. No. 09/622,452, which are each incorporated herein by reference in their entireties. Other examples of RANTES constructs and sequences are disclosed in PCT application no. PCT/US11/024098, which is incorporated herein by reference in its entirety. Examples of chemokines CTACK, TECK and MEC constructs and sequences are disclosed in PCT application no. PCT/US2005/042231 and corresponding U.S. application Ser. No. 11/719,646, which are each incorporated herein by reference in their entireties. Examples of OX40 and other immunomodulators are disclosed in U.S. application Ser. No. 10/560,653, which is incorporated herein by reference in its entirety. Examples of DR5 and other immunomodulators are disclosed in U.S. application Ser. No. 09/622,452, which is incorporated herein by reference in its entirety.

The vaccine may further comprise a genetic vaccine facilitator agent as described in U.S. Ser. No. 021,579 filed Apr. 1, 1994, which is fully incorporated by reference in its entirety.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

In addition to using genetic vaccines such as DNA vaccines, coding sequences and or proteins may be incorporated into to attenuated live vaccines, recombinant vectors or subunit vaccines. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference.

6. Methods of Delivery the Vaccine

Provided herein is a method for delivering the vaccine that provides genetic constructs that encode MRSA PBP2a protein against which an immune response can be induced. The method of delivering the vaccine or vaccination may be provided to induce a therapeutic and prophylactic immune response. The vaccination process may generate in the mammal an immune response against MRSA. The delivery of the vaccine may include transfection of the a nucleic acid molecule that includes the coding sequence that encode MRSA PBP2a protein which results in high levels of expression in the cell. The MRSA PBP2a protein or peptides of it are delivered to the surface of the cell and/or secreted by it upon which the immune system recognized and induces a cellular, humoral, or cellular and humoral response. The delivery of the vaccine may be use to induce or elicit and immune response in mammals against MRSA by administering to the mammals the vaccine as discussed above.

Upon delivery of the vaccine and plasmid into the cells of the mammal, the transfected cells will express the coding sequences and secrete the MRSA PBP2a protein. The proteins will be recognized as foreign by the immune system and antibodies will be made against them. These antibodies will be maintained by the immune system and allow for an effective response against ongoing MRSA infection and subsequent MRSA infections.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins and/or genes encoding α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of IL-12, IL-15, IL-28, CTACK, TECK, MEC and RANTES or functional fragments thereof, and proteins selected from the group consisting of: IL-12 protein, IL-15 protein, IL-28 protein, CTACK protein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, U.S. provisional application Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The high mortality rate in association with the fact that MRSA infections are on the rise prompted efforts to generate a vaccine capable of inducing immunity to the MRSA-specific PBP2a protein. To that end, two PBP2a DNA vaccine antigens were initially constructed: one consisting of only the catalytic domain of PBP2a linked to the IgE signal peptide sequence (SEQ ID NO:12, hereafter referred to as “Short” encoded by SEQ ID NO:11) and one consisting of the entire PBP2a protein save for the transmembrane domain linked to the IgE signal peptide sequence (SEQ ID NO:10, hereafter referred to as “No Anchor” encoded by SEQ ID NO:9). The inclusion of the IgE signal peptide sequence provides a high efficiency signal peptide sequence. Coding sequences were codon optimized and RNA optimized to further increase expression levels.

Figure 2:
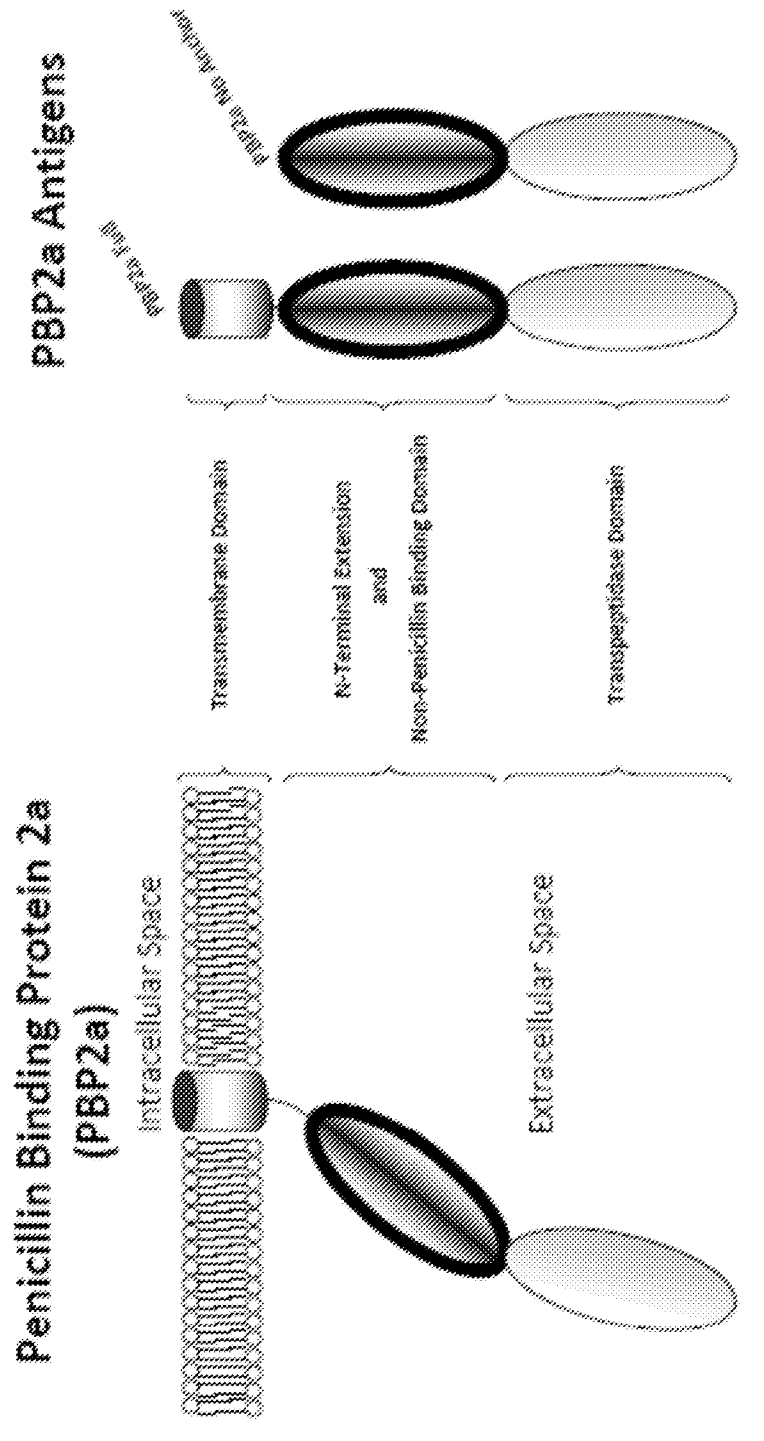
FIG. 2 shows data of titers of PBP2a-specific antibodies in mice immunized with a DNA vaccine that encodes a "Short" PBP2a Protein fragment compared to PBP2a-specific antibodies in mice immunized with a DNA vaccine that encodes a "No Anchor" PBP2a Protein fragment.

Mice were immunized with 25 ug of either the Short or No Anchor vaccine variant in the quadriceps muscle followed by electroporation with the Cellectra device from Inovio Biomedical. Two weeks after the single immunization mice were bled and sera was tested for PBP2a-specific antibodies. The group of animals receiving the Short variant showed a greater than 3-fold increase in antibodies titers as compared with the pre-immune sera from this group, while the animals receiving the No Anchor vaccine variant showed an increase of over 6-fold (FIG. 2). These data shows that these plasmid antigens are able to elicit in vivo PBP2a-specific antibody responses two weeks after a single immunization. These data support the use of such immunogen designs as a therapeutic approach for this important infectious disease.

Example 2

Figure 3:
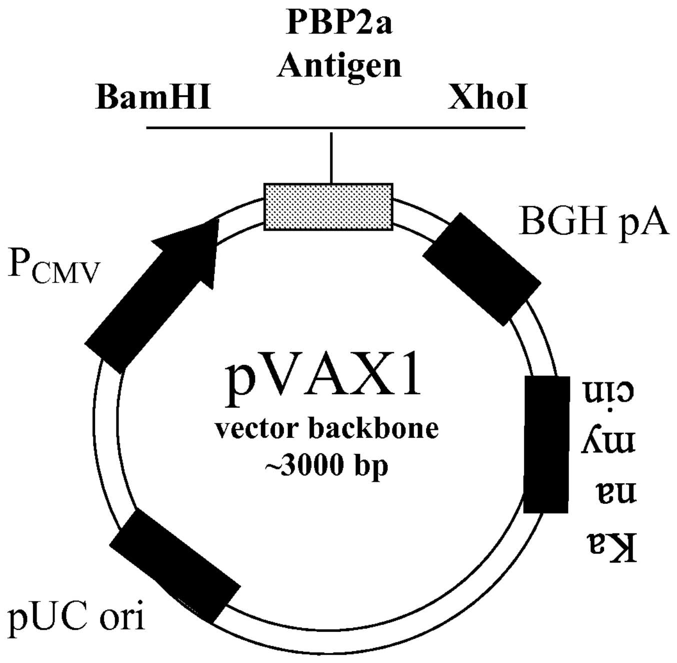
FIG. 3 shows a diagram of backbone plasmid pVax1 with insert of PBP2a coding sequences cloned to be operably linked to the CMV promoter and BGH polyA site.

A construct was made which includes a full-length variant of the PBP2a protein including the transmembrane domain. The full length MRSA PBP2a protein DNA vaccine construct, which comprises coding sequence of the full length PBP2a protein (SEQ ID NO:2) linked to the IgE signal peptide sequence (SEQ ID NO:13), is hereafter referred to as “Full” encoded by SEQ ID NO:7) and has the amino acid sequence SEQ ID NO:8. FIG. 3 shows a diagram of backbone plasmid pVax1 with insert of PBP2a coding sequences cloned to be operably linked to the CMV promoter and BGH polyA site.

Example 3

Figure 4:
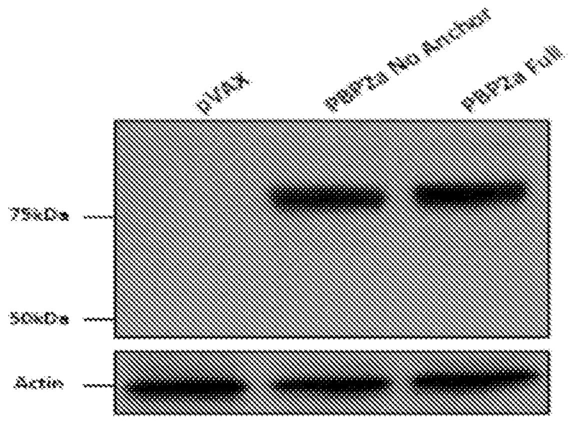
FIG. 4 shows results from expression experiments comparing protein expression levels using pVax as a control and constructs which encode Full and No Anchor versions of the PBP2a protein.

FIG. 4 shows results from expression experiments comparing protein expression levels using pVax as a control and plasmids comprising constructs which encode Full and No Anchor versions of the PBP2a protein.

Immune responses generated by plasmids comprising constructs which encode Full and No Anchor versions of the PBP2a protein were compared. Mice were bled and immunized on day 0 with 25 μg of either the pVax, Full (SEQ ID NO:7) or No Anchor vaccine (SEQ ID NO:9) variant in the quadriceps muscle followed by electroporation with the Cellectra device from Inovio Biomedical. Two weeks later, mice were bled and received a second immunization. On day 28, mice were bled and analyzed by ELISA, Serum Bactericidal Assay and Opsonization Phagocytosis and Killing Assay.

Figure 5:
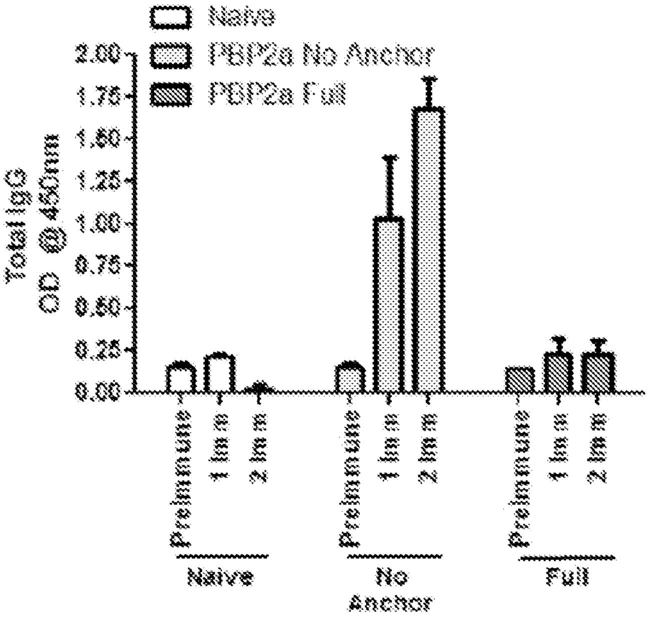
FIG. 5 shows composite data of anti-PBP2a IgG titers at day 0, day 14 and day 28 from naïve/control mice or mice vaccinated with Full or No Anchor vaccine mice at day 0 and day 14.
Figure 6:
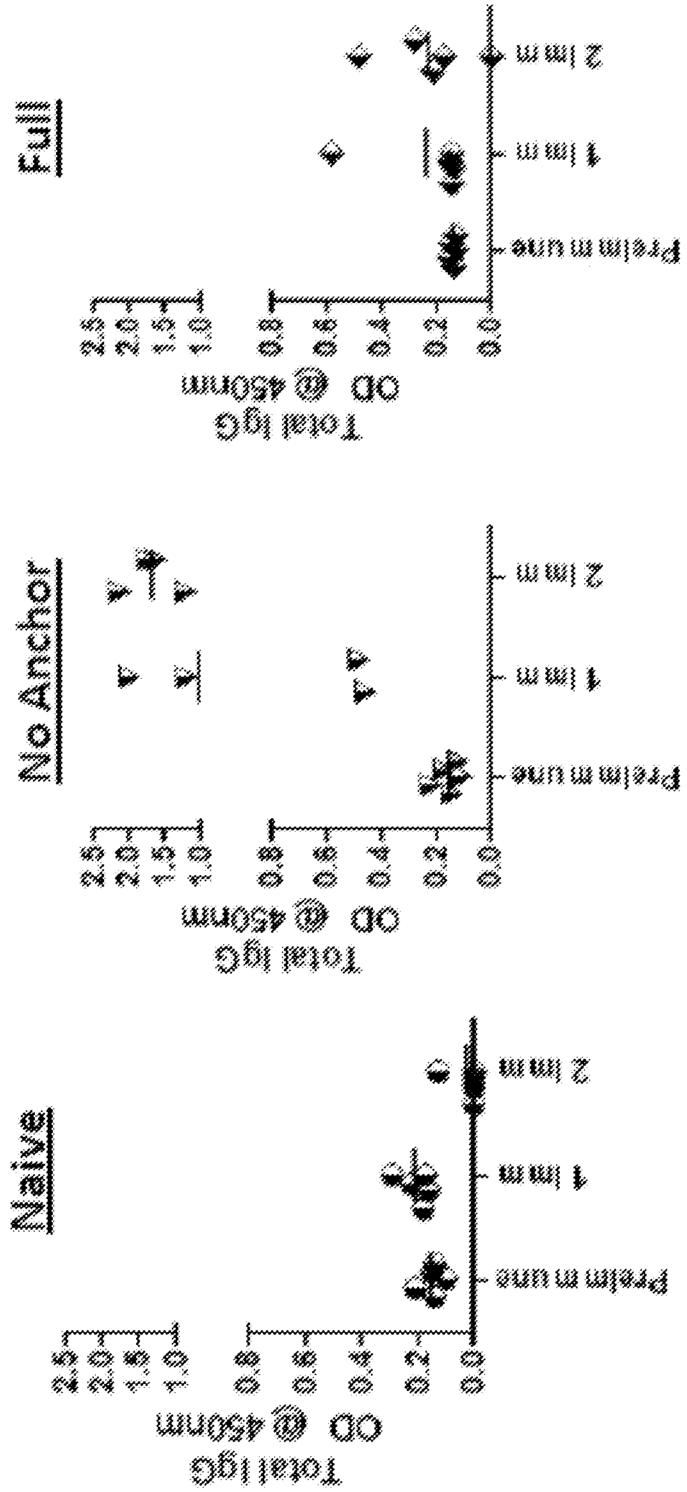
FIG. 6 shows individual data of anti-PBP2a IgG titers at day 0, day 14 and day 28 from naïve/control mice (left) or mice vaccinated with No Anchor (center) or Full (right) vaccine mice at day 0 and day 14.

Titers of PBP2a-specific IgG antibodies in sera taken at day 0, day 14 and day 28 from naïve/control mice or mice vaccinated with Full or No Anchor vaccine mice at day 0 and day 14 were compared. Composite results are shown in FIG. 5. FIG. 6 shows individual data of anti-PBP2a IgG titers at day 0, day 14 and day 28 from naïve/control mice (left) or mice vaccinated with No Anchor (center) or Full (right) vaccine mice at day 0 and day 14.

Figure 7:
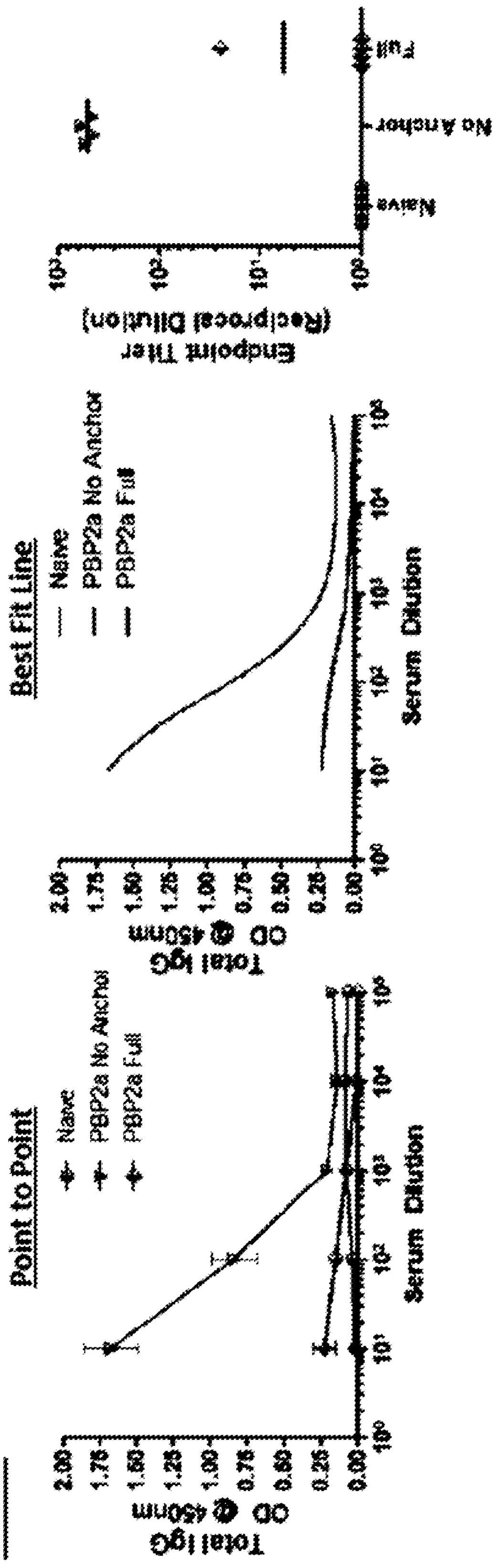
FIG. 7 shows a comparison of data from naïve/control mice or mice vaccinated with Full or No Anchor using point to point (left) and best fit (center) graphing of data of titers of IgG in sera dilutions and endpoint titers of reciprocal dilutions (right)

Titers of PBP2a-specific IgG antibodies in diluted sera from naïve/control mice or mice vaccinated with Full or No Anchor were measured and data is shown in FIG. 7 in which data was plotted using point to point graphing (left) and best fit graphing (center). Endpoint titers of reciprocal dilutions are also shown in FIG. 7 (right).

Figure 8:
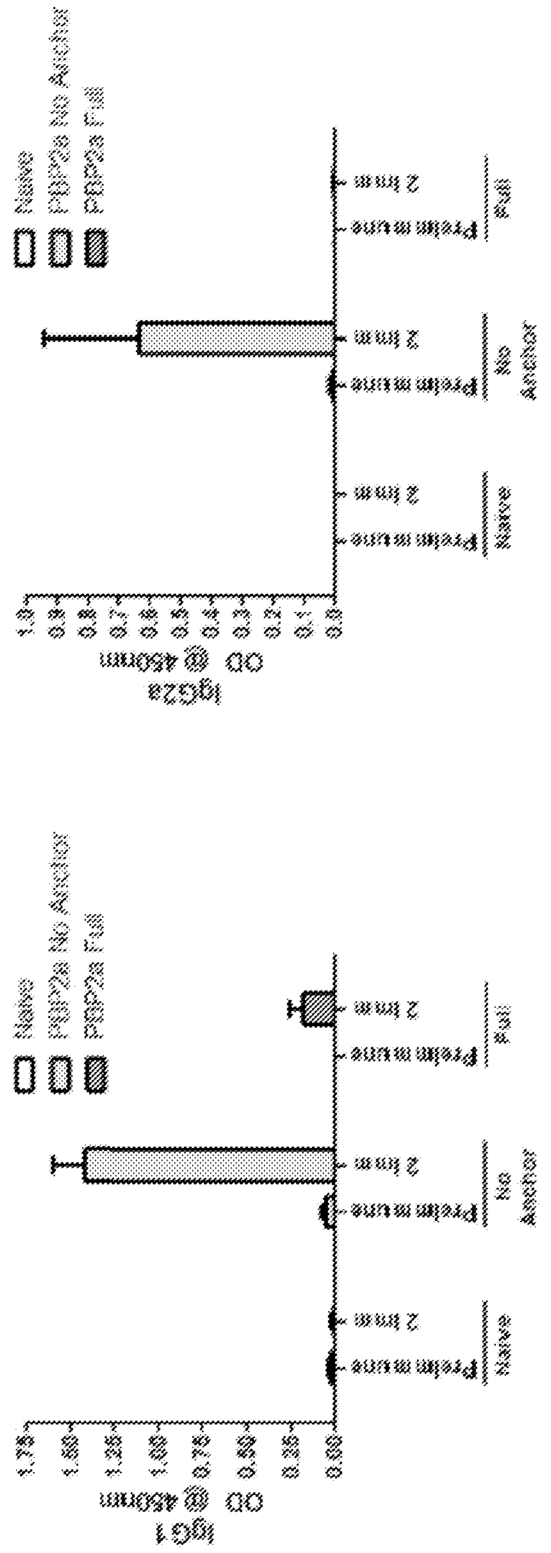
FIG. 8 shows separate titers at day 0 and day 28 for IgG1 (left) and IgG2a (right) from naïve/control mice or mice vaccinated with Full or No Anchor at day 0 and day 14.

Separate titers for IgG1 and IgG2a in sera taken at day 0 and day 28 from naïve/control mice or mice vaccinated with Full or No Anchor on days 0 and 14. Results showing IgG1 titers are shown in FIG. 8 on left; results showing IgG2a titers are shown in FIG. 8 on right.

Example 4

Additional studies were carried out in which Guinea Pigs were immunized with 100 ug intradermally (ID). Three and six weeks after completion of immunization, animals were bled and sera was tested for PBP2a-specific antibodies. Both the Full and No Anchor variants drove robust endpoint titers three weeks after immunization which approached $10^6$ for the Full variant and approaching $10^4$ for the No Anchor variant. Six weeks post immunization the titers remained largely consistent, suggesting a durability of response.

Figure 9:
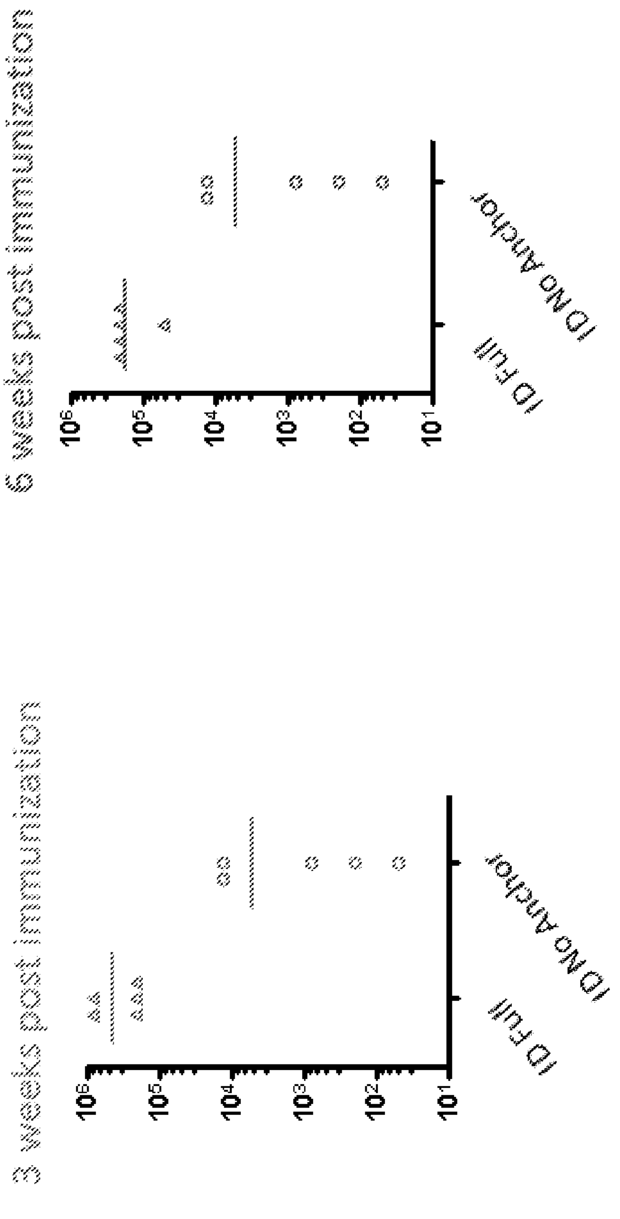
FIG. 9 depicts IgG titers taken from Guinea Pigs immunized intradermally (ID) with the Full or No Anchor variants.

FIG. 9 depicts IgG titers taken from Guinea Pigs immunized intradermally (ID) with the Full or No Anchor variants. Animals were immunized three times in the skin at three week intervals. Three (left graph) and six (right graph) weeks after the final immunization, animals were bled and titers specific to the PBP2a antigen were measured.

The invention claimed is:

1. A composition comprising a nucleic acid molecule that encodes a Methicillin-resistant *Staphylococcus aureus* (MRSA) penicillin-binding protein 2a (PBP2a) protein or a fragment thereof which comprises at least 245 amino acid, the nucleic acid molecule comprising:

an optimized nucleic acid sequence that is at least 98% identical to SEQ ID NO:1 and that encodes a consensus protein at least 98% identical to SEQ ID NO:2; or an optimized nucleic acid sequence that is at least 98% identical to a fragment of SEQ ID NO:1 and that encodes a fragment of a consensus protein at least 98% identical to SEQ ID NO:2, wherein the fragment encodes an immunogenic fragment of a protein that is 98% identical to a fragment of SEQ ID NO:2 comprising at least 245 amino acids;

wherein the composition further comprises a nucleic acid sequence that encodes one or more proteins selected from the group consisting of: IL-12, IL-15 and IL-28.

2. The nucleic acid molecule of claim 1 comprising a fragment of a nucleic acid sequence that is at least 98% identical to SEQ ID NO:1 and that encodes a protein at least 98% identical to SEQ ID NO:2, wherein the fragment encodes an immunogenic fragment of a protein that is 98% identical to a fragment of SEQ ID NO:2 that comprises at least 245 amino acids.

3. The nucleic acid molecule of claim 2 comprising a fragment of a nucleic acid sequence that is at least 98% identical to SEQ ID NO:1 and that encodes a protein at least 98% identical to SEQ ID NO:2, wherein the fragment encodes an immunogenic fragment of SEQ ID NO:2 having at least 245 amino acids.

4. The nucleic acid molecule of claim 2 wherein the fragment is a fragment of SEQ ID NO:1.

5. The nucleic acid molecule of claim 2 comprising SEQ ID NO:5.

6. The nucleic acid molecule of claim 2 comprising SEQ ID NO:3.

7. The nucleic acid molecule of claim 2 wherein an immunogenic fragment of a protein that is 98% identical to a fragment of SEQ ID NO:2 comprises at least 245 amino acids is free of coding sequences that encode an MRSA PBP2a transmembrane domain.

8. The nucleic acid molecule of claim 1 comprising a coding sequence that encodes a signal peptide sequence operable linked to the nucleic acid sequence that is at least 98% identical to SEQ ID NO:1 and that encodes a protein at least 98% identical to SEQ ID NO:2; or the fragment of a nucleic acid sequence that is at least 98% identical to SEQ ID NO:1 and that encodes a protein at least 98% identical to SEQ ID NO:2.

9. The nucleic acid molecule of claim 8 wherein the signal peptide sequence is an IgE signal peptide sequence SEQ ID NO:13.

10. The nucleic acid molecule of claim 9 comprising sequence SEQ ID NO:11.

11. The nucleic acid molecule of claim 9 comprising sequence SEQ ID NO:9.

12. The nucleic acid molecule of claim 9 comprising a nucleic acid sequence that is at least 98% identical to SEQ ID NO:1 and that encodes a protein at least 98% identical to SEQ ID NO:2.

13. The nucleic acid molecule of claim 12 comprising a nucleic acid sequence that is at least 98% identical to SEQ ID NO:1 and that encodes SEQ ID NO:2.

14. The nucleic acid molecule of claim 12 comprising SEQ ID NO:1.

15. The nucleic acid molecule of claim 9 comprising SEQ ID NO:7.

16. The nucleic acid molecule of claim 1 wherein the nucleic acid molecule is a plasmid.

17. The nucleic acid molecule of claim 1 wherein the nucleic acid molecule is an expression vector and sequences encoding said one more proteins are operable linked to regulatory elements.

18. The nucleic acid molecule of claim 1 wherein the nucleic acid molecule is incorporated into a viral particle.

* * * * *

SEQUENCE LISTING

```
<160> NUMBER OF SEQ ID NOS: 13

<210> SEQ ID NO 1
<211> LENGTH: 2004
<212> TYPE: DNA
<213> ORGANISM: Artificial Sequence
<220> FEATURE:
<223> OTHER INFORMATION: MRSA consensus nucleic acid

<400> SEQUENCE: 1

aaaaagatca agattgtgcc tctgattctg attgtggtcg tggtcggatt cggcatctac      60

ttctacgcaa gcaaggacaa agagatcaac aatactatcg acgccattga agataagaac     120

ttcaaacagg tgtacaaaga cagctcctat atctcaaaga gcgataatgg agaggtcgaa     180

atgacagagc gccccatcaa aatctacaac tccctgggcg tgaaggacat caacatccag     240

gataggaaaa tcaagaaagt gtctaagaac aagaaacgcg tcgatgccca gtacaagatc     300

aagaccaact atggcaatat cgaccgaaac gtgcagttca attttgtcaa agaggatggc     360

atgtggaagc tggactggga tcactctgtg atcattcctg ggatgcagaa ggaccagtca     420

atccatattg agaatctgaa aagcgaacgg ggcaagatcc tggatagaaa caatgtggag     480

ctggccaaca caggcactgc ttacgaaatc gggattgtgc ctaagaatgt cagcaagaaa     540

gactacaagg ccatcgctaa agagctgtcc atctctgaag actatatcaa gcagcagatg     600

gatcagaact gggtgcagga cgataccttt gtgccactga agacagtcaa gaaaatggac     660

gagtacctga gcgatttcgc caagaaattt cacctgacca caaacgagac tgaaagtagg     720

aattaccccc tgggcaaggc tacctcacat ctgctgggct atgtgggacc tattaactcc     780

gaggaactga agcagaaaga gtacaagggg tataaagacg atgccgtgat cggcaagaaa     840

gggctggaga agctgtacga caagaaactg cagcacgaag atggatatcg ggtgaccatc     900

gtcgacgata acagcaatac catcgcacat acactgattg agaagaaaaa gaaagacggc     960

aaagatatcc agctgacaat tgacgctaag gtgcagaagt ctatctacaa caacatgaag    1020

aacgattatg ggagtggaac tgccatccac ccacagaccg gggaactgct ggctctggtg    1080

agtacaccat catacgacgt gtacccette atgtacggaa tgtccaacga ggaatataac    1140

aagctgactg aggataagaa agaacctctg ctgaataagt ttcagattac taccagccca    1200

gggtccactc agaaaatcct gaccgccatg attggactga acaataagac actggacgat    1260
```

-continued

```
aagacttcat acaaaatcga cggcaagggg tggcagaagg ataaaagctg gggcgggtac   1320

aacgtgacca gatatgaggt ggtcaacggc aatatcgacc tgaagcaggc catcgaatct   1380

agtgataaca tcttctttgc aagggtcgcc ctggagctgg gatctaagaa attcgaaaag   1440

ggcatgaaga aactgggagt gggcgaggac atccccagcg attacccttt ttataacgct   1500

cagatttcca acaagaatct ggacaatgag atcctgctgg cagatagtgg gtacggacag   1560

ggcgaaatcc tgattaaccc agtgcagatc ctgtctatct acagtgcact ggagaacaat   1620

gggaacatta atgcccctca cctgctgaag gacaccaaga acaaagtgtg gaagaaaaat   1680

atcatcagca aggagaacat caatctgctg acagacggca tgcagcaggt ggtcaacaag   1740

actcataaag aagatatcta ccgatcctat gctaatctga tcggaaagtc tggcaccgca   1800

gagctgaaga tgaaacaggg ggaaacagga cggcagatcg ggtggttcat tagttacgac   1860

aaggataacc ctaatatgat gatggccatt aacgtgaaag acgtgcagga taagggaatg   1920

gcttcatata atgcaaagat ctcaggaaaa gtgtatgacg aactgtatga aaatgggaac   1980

aaaaagtatg acattgacga atga                                          2004
```

<210> SEQ ID NO 2
<211> LENGTH: 667
<212> TYPE: PRT
<213> ORGANISM: Artificial Sequence
<220> FEATURE:
<223> OTHER INFORMATION: MRSA consensus amino acid sequence

<400> SEQUENCE: 2

```
Lys Lys Ile Lys Ile Val Pro Leu Ile Leu Ile Val Val Val Val Gly
1               5                   10                  15

Phe Gly Ile Tyr Phe Tyr Ala Ser Lys Asp Lys Glu Ile Asn Asn Thr
            20                  25                  30

Ile Asp Ala Ile Glu Asp Lys Asn Phe Lys Gln Val Tyr Lys Asp Ser
        35                  40                  45

Ser Tyr Ile Ser Lys Ser Asp Asn Gly Glu Val Glu Met Thr Glu Arg
    50                  55                  60

Pro Ile Lys Ile Tyr Asn Ser Leu Gly Val Lys Asp Ile Asn Ile Gln
65                  70                  75                  80

Asp Arg Lys Ile Lys Lys Val Ser Lys Asn Lys Lys Arg Val Asp Ala
                85                  90                  95

Gln Tyr Lys Ile Lys Thr Asn Tyr Gly Asn Ile Asp Arg Asn Val Gln
            100                 105                 110

Phe Asn Phe Val Lys Glu Asp Gly Met Trp Lys Leu Asp Trp Asp His
        115                 120                 125

Ser Val Ile Ile Pro Gly Met Gln Lys Asp Gln Ser Ile His Ile Glu
    130                 135                 140

Asn Leu Lys Ser Glu Arg Gly Lys Ile Leu Asp Arg Asn Asn Val Glu
145                 150                 155                 160

Leu Ala Asn Thr Gly Thr Ala Tyr Glu Ile Gly Ile Val Pro Lys Asn
                165                 170                 175

Val Ser Lys Lys Asp Tyr Lys Ala Ile Ala Lys Glu Leu Ser Ile Ser
            180                 185                 190

Glu Asp Tyr Ile Lys Gln Gln Met Asp Gln Asn Trp Val Gln Asp Asp
        195                 200                 205

Thr Phe Val Pro Leu Lys Thr Val Lys Lys Met Asp Glu Tyr Leu Ser
    210                 215                 220

Asp Phe Ala Lys Lys Phe His Leu Thr Thr Asn Glu Thr Glu Ser Arg
```

```
225                 230                 235                 240

Asn Tyr Pro Leu Gly Lys Ala Thr Ser His Leu Leu Gly Tyr Val Gly
                245                 250                 255

Pro Ile Asn Ser Glu Glu Leu Lys Gln Lys Glu Tyr Lys Gly Tyr Lys
            260                 265                 270

Asp Asp Ala Val Ile Gly Lys Lys Gly Leu Glu Lys Leu Tyr Asp Lys
        275                 280                 285

Lys Leu Gln His Glu Asp Gly Tyr Arg Val Thr Ile Val Asp Asp Asn
    290                 295                 300

Ser Asn Thr Ile Ala His Thr Leu Ile Glu Lys Lys Lys Lys Asp Gly
305                 310                 315                 320

Lys Asp Ile Gln Leu Thr Ile Asp Ala Lys Val Gln Lys Ser Ile Tyr
                325                 330                 335

Asn Asn Met Lys Asn Asp Tyr Gly Ser Gly Thr Ala Ile His Pro Gln
            340                 345                 350

Thr Gly Glu Leu Leu Ala Leu Val Ser Thr Pro Ser Tyr Asp Val Tyr
        355                 360                 365

Pro Phe Met Tyr Gly Met Ser Asn Glu Glu Tyr Asn Lys Leu Thr Glu
    370                 375                 380

Asp Lys Lys Glu Pro Leu Leu Asn Lys Phe Gln Ile Thr Thr Ser Pro
385                 390                 395                 400

Gly Ser Thr Gln Lys Ile Leu Thr Ala Met Ile Gly Leu Asn Asn Lys
                405                 410                 415

Thr Leu Asp Asp Lys Thr Ser Tyr Lys Ile Asp Gly Lys Gly Trp Gln
            420                 425                 430

Lys Asp Lys Ser Trp Gly Gly Tyr Asn Val Thr Arg Tyr Glu Val Val
        435                 440                 445

Asn Gly Asn Ile Asp Leu Lys Gln Ala Ile Glu Ser Ser Asp Asn Ile
    450                 455                 460

Phe Phe Ala Arg Val Ala Leu Glu Leu Gly Ser Lys Lys Phe Glu Lys
465                 470                 475                 480

Gly Met Lys Lys Leu Gly Val Gly Glu Asp Ile Pro Ser Asp Tyr Pro
                485                 490                 495

Phe Tyr Asn Ala Gln Ile Ser Asn Lys Asn Leu Asp Asn Glu Ile Leu
            500                 505                 510

Leu Ala Asp Ser Gly Tyr Gly Gln Gly Glu Ile Leu Ile Asn Pro Val
        515                 520                 525

Gln Ile Leu Ser Ile Tyr Ser Ala Leu Glu Asn Asn Gly Asn Ile Asn
    530                 535                 540

Ala Pro His Leu Leu Lys Asp Thr Lys Asn Lys Val Trp Lys Lys Asn
545                 550                 555                 560

Ile Ile Ser Lys Glu Asn Ile Asn Leu Leu Thr Asp Gly Met Gln Gln
                565                 570                 575

Val Val Asn Lys Thr His Lys Glu Asp Ile Tyr Arg Ser Tyr Ala Asn
            580                 585                 590

Leu Ile Gly Lys Ser Gly Thr Ala Glu Leu Lys Met Lys Gln Gly Glu
        595                 600                 605

Thr Gly Arg Gln Ile Gly Trp Phe Ile Ser Tyr Asp Lys Asp Asn Pro
    610                 615                 620

Asn Met Met Met Ala Ile Asn Val Lys Asp Val Gln Asp Lys Gly Met
625                 630                 635                 640

Ala Ser Tyr Asn Ala Lys Ile Ser Gly Lys Val Tyr Asp Glu Leu Tyr
                645                 650                 655
```

Glu Asn Gly Asn Lys Lys Tyr Asp Ile Asp Glu
660 665

<210> SEQ ID NO 3
<211> LENGTH: 1935
<212> TYPE: DNA
<213> ORGANISM: Artificial Sequence
<220> FEATURE:
<223> OTHER INFORMATION: MRSA fragment 1 nucleic acid

<400> SEQUENCE: 3
agcaaggaca aagagatcaa caatactatc gacgccattg aagataagaa cttcaaacag 60
gtgtacaaag acagctccta tatctcaaag agcgataatg gagaggtcga aatgacagag 120
cgccccatca aaatctacaa ctccctgggc gtgaaggaca tcaacatcca ggataggaaa 180
atcaagaaag tgtctaagaa caagaaacgc gtcgatgccc agtacaagat caagaccaac 240
tatggcaata tcgaccgaaa cgtgcagttc aattttgtca aagaggatgg catgtggaag 300
ctggactggg atcactctgt gatcattcct gggatgcaga aggaccagtc aatccatatt 360
gagaatctga aaagcgaacg gggcaagatc ctggatagaa acaatgtgga gctggccaac 420
acaggcactg cttacgaaat cgggattgtg cctaagaatg tcagcaagaa agactacaag 480
gccatcgcta aagagctgtc catctctgaa gactatatca agcagcagat ggatcagaac 540
tgggtgcagg acgatacctt tgtgccactg aagacagtca agaaaatgga cgagtacctg 600
agcgatttcg ccaagaaatt tcacctgacc acaaacgaga ctgaaagtag gaattacccc 660
ctgggcaagg ctacctcaca tctgctgggc tatgtgggac ctattaactc cgaggaactg 720
aagcagaaag agtacaaggg gtataaagac gatgccgtga tcggcaagaa agggctggag 780
aagctgtacg acaagaaact gcagcacgaa gatggatatc gggtgaccat cgtcgacgat 840
aacagcaata ccatcgcaca tacactgatt gagaagaaaa agaaagacgg caaagatatc 900
cagctgacaa ttgacgctaa ggtgcagaag tctatctaca acaacatgaa gaacgattat 960
gggagtggaa ctgccatcca cccacagacc ggggaactgc tggctctggt gagtacacca 1020
tcatacgacg tgtacccctt catgtacgga atgtccaacg aggaatataa caagctgact 1080
gaggataaga aagaacctct gctgaataag tttcagatta ctaccagccc agggtccact 1140
cagaaaatcc tgaccgccat gattggactg aacaataaga cactggacga taagacttca 1200
tacaaaatcg acggcaaggg gtggcagaag gataaaagct ggggcgggta caacgtgacc 1260
agatatgagg tggtcaacgg caatatcgac ctgaagcagg ccatcgaatc tagtgataac 1320
atcttctttg caagggtcgc cctggagctg ggatctaaga aattcgaaaa gggcatgaag 1380
aaactgggag tgggcgagga catccccagc gattaccctt tttataacgc tcagatttcc 1440
aacaagaatc tggacaatga gatcctgctg gcagatagtg ggtacggaca gggcgaaatc 1500
ctgattaacc cagtgcagat cctgtctatc tacagtgcac tggagaacaa tgggaacatt 1560
aatgcccctc acctgctgaa ggacaccaag aacaaagtgt ggaagaaaaa tatcatcagc 1620
aaggagaaca tcaatctgct gacagacggc atgcagcagg tggtcaacaa gactcataaa 1680
gaagatatct accgatccta tgctaatctg atcggaaagt ctggcaccgc agagctgaag 1740
atgaaacagg gggaaacagg acggcagatc gggtggttca ttagttacga caaggataac 1800
cctaatatga tgatggccat taacgtgaaa gacgtgcagg ataagggaat ggcttcatat 1860
aatgcaaaga tctcaggaaa agtgtatgac gaactgtatg aaaatggaaa taagaaatat 1920
gacattgacg aatga 1935

<210> SEQ ID NO 4
<211> LENGTH: 644
<212> TYPE: PRT
<213> ORGANISM: Artificial Sequence
<220> FEATURE:
<223> OTHER INFORMATION: MRSA fragment 2 amino acid

<400> SEQUENCE: 4

```
Ser Lys Asp Lys Glu Ile Asn Asn Thr Ile Asp Ala Ile Glu Asp Lys
1               5                   10                  15

Asn Phe Lys Gln Val Tyr Lys Asp Ser Ser Tyr Ile Ser Lys Ser Asp
            20                  25                  30

Asn Gly Glu Val Glu Met Thr Glu Arg Pro Ile Lys Ile Tyr Asn Ser
        35                  40                  45

Leu Gly Val Lys Asp Ile Asn Ile Gln Asp Arg Lys Ile Lys Lys Val
    50                  55                  60

Ser Lys Asn Lys Lys Arg Val Asp Ala Gln Tyr Lys Ile Lys Thr Asn
65                  70                  75                  80

Tyr Gly Asn Ile Asp Arg Asn Val Gln Phe Asn Phe Val Lys Glu Asp
                85                  90                  95

Gly Met Trp Lys Leu Asp Trp Asp His Ser Val Ile Ile Pro Gly Met
            100                 105                 110

Gln Lys Asp Gln Ser Ile His Ile Glu Asn Leu Lys Ser Glu Arg Gly
        115                 120                 125

Lys Ile Leu Asp Arg Asn Asn Val Glu Leu Ala Asn Thr Gly Thr Ala
    130                 135                 140

Tyr Glu Ile Gly Ile Val Pro Lys Asn Val Ser Lys Lys Asp Tyr Lys
145                 150                 155                 160

Ala Ile Ala Lys Glu Leu Ser Ile Ser Glu Asp Tyr Ile Lys Gln Gln
                165                 170                 175

Met Asp Gln Asn Trp Val Gln Asp Asp Thr Phe Val Pro Leu Lys Thr
            180                 185                 190

Val Lys Lys Met Asp Glu Tyr Leu Ser Asp Phe Ala Lys Lys Phe His
        195                 200                 205

Leu Thr Thr Asn Glu Thr Glu Ser Arg Asn Tyr Pro Leu Gly Lys Ala
    210                 215                 220

Thr Ser His Leu Leu Gly Tyr Val Gly Pro Ile Asn Ser Glu Glu Leu
225                 230                 235                 240

Lys Gln Lys Glu Tyr Lys Gly Tyr Lys Asp Asp Ala Val Ile Gly Lys
                245                 250                 255

Lys Gly Leu Glu Lys Leu Tyr Asp Lys Lys Leu Gln His Glu Asp Gly
            260                 265                 270

Tyr Arg Val Thr Ile Val Asp Asp Asn Ser Asn Thr Ile Ala His Thr
        275                 280                 285

Leu Ile Glu Lys Lys Lys Lys Asp Gly Lys Asp Ile Gln Leu Thr Ile
    290                 295                 300

Asp Ala Lys Val Gln Lys Ser Ile Tyr Asn Asn Met Lys Asn Asp Tyr
305                 310                 315                 320

Gly Ser Gly Thr Ala Ile His Pro Gln Thr Gly Glu Leu Leu Ala Leu
                325                 330                 335

Val Ser Thr Pro Ser Tyr Asp Val Tyr Pro Phe Met Tyr Gly Met Ser
            340                 345                 350

Asn Glu Glu Tyr Asn Lys Leu Thr Glu Asp Lys Lys Glu Pro Leu Leu
        355                 360                 365
```

```
Asn Lys Phe Gln Ile Thr Thr Ser Pro Gly Ser Thr Gln Lys Ile Leu
    370                 375                 380

Thr Ala Met Ile Gly Leu Asn Asn Lys Thr Leu Asp Asp Lys Thr Ser
385                 390                 395                 400

Tyr Lys Ile Asp Gly Lys Gly Trp Gln Lys Asp Lys Ser Trp Gly Gly
                405                 410                 415

Tyr Asn Val Thr Arg Tyr Glu Val Val Asn Gly Asn Ile Asp Leu Lys
            420                 425                 430

Gln Ala Ile Glu Ser Ser Asp Asn Ile Phe Phe Ala Arg Val Ala Leu
        435                 440                 445

Glu Leu Gly Ser Lys Lys Phe Glu Lys Gly Met Lys Lys Leu Gly Val
    450                 455                 460

Gly Glu Asp Ile Pro Ser Asp Tyr Pro Phe Tyr Asn Ala Gln Ile Ser
465                 470                 475                 480

Asn Lys Asn Leu Asp Asn Glu Ile Leu Leu Ala Asp Ser Gly Tyr Gly
                485                 490                 495

Gln Gly Glu Ile Leu Ile Asn Pro Val Gln Ile Leu Ser Ile Tyr Ser
            500                 505                 510

Ala Leu Glu Asn Asn Gly Asn Ile Asn Ala Pro His Leu Leu Lys Asp
        515                 520                 525

Thr Lys Asn Lys Val Trp Lys Lys Asn Ile Ile Ser Lys Glu Asn Ile
    530                 535                 540

Asn Leu Leu Thr Asp Gly Met Gln Gln Val Val Asn Lys Thr His Lys
545                 550                 555                 560

Glu Asp Ile Tyr Arg Ser Tyr Ala Asn Leu Ile Gly Lys Ser Gly Thr
                565                 570                 575

Ala Glu Leu Lys Met Lys Gln Gly Glu Thr Gly Arg Gln Ile Gly Trp
            580                 585                 590

Phe Ile Ser Tyr Asp Lys Asp Asn Pro Asn Met Met Met Ala Ile Asn
        595                 600                 605

Val Lys Asp Val Gln Asp Lys Gly Met Ala Ser Tyr Asn Ala Lys Ile
    610                 615                 620

Ser Gly Lys Val Tyr Asp Glu Leu Tyr Glu Asn Gly Asn Lys Lys Tyr
625                 630                 635                 640

Asp Ile Asp Glu
```

<210> SEQ ID NO 5
<211> LENGTH: 729
<212> TYPE: DNA
<213> ORGANISM: Artificial Sequence
<220> FEATURE:
<223> OTHER INFORMATION: MRSA fragment 3 nucleic acid

<400> SEQUENCE: 5

```
atcgacggca aggggtggca gaaggataaa agctggggcg ggtacaacgt gaccagatat      60

gaggtggtca acggcaatat cgacctgaag caggccatcg aatctagtga taacatcttc     120

tttgcaaggg tcgccctgga gctgggatct aagaaattcg aaaagggcat gaagaaactg     180

ggagtgggcg aggacatccc cagcgattac cctttttata acgctcagat ttccaacaag     240

aatctggaca atgagatcct gctggcagat agtgggtacg gacagggcga aatcctgatt     300

aacccagtgc agatcctgtc tatctacagt gcactggaga acaatgggaa cattaatgcc     360

cctcacctgc tgaaggacac caagaacaaa gtgtggaaga aaaatatcat cagcaaggag     420

aacatcaatc tgctgacaga cggcatgcag caggtggtca acaagactca taaagaagat     480
```

-continued atctaccgat cctatgctaa tctgatcgga aagtctggca ccgcagagct gaagatgaaa 540 caggggggaaa caggacggca gatcgggtgg ttcattagtt acgacaagga taaccctaat 600
atgatgatgg ccattaacgt gaaagacgtg caggataagg gaatggcttc atataatgca 660
aagatctcag gaaaagtgta tgacgaactg tatgaaaatg ggaacaaaaa gtatgacatt 720
gacgaatga 729

<210> SEQ ID NO 6
<211> LENGTH: 242
<212> TYPE: PRT
<213> ORGANISM: Artificial Sequence
<220> FEATURE:
<223> OTHER INFORMATION: MRSA fragment 4 amino acid

<400> SEQUENCE: 6

Ile Asp Gly Lys Gly Trp Gln Lys Asp Lys Ser Trp Gly Gly Tyr Asn
1 5 10 15

Val Thr Arg Tyr Glu Val Val Asn Gly Asn Ile Asp Leu Lys Gln Ala
20 25 30

Ile Glu Ser Ser Asp Asn Ile Phe Phe Ala Arg Val Ala Leu Glu Leu
35 40 45

Gly Ser Lys Lys Phe Glu Lys Gly Met Lys Lys Leu Gly Val Gly Glu
50 55 60

Asp Ile Pro Ser Asp Tyr Pro Phe Tyr Asn Ala Gln Ile Ser Asn Lys
65 70 75 80

Asn Leu Asp Asn Glu Ile Leu Leu Ala Asp Ser Gly Tyr Gly Gln Gly
85 90 95

Glu Ile Leu Ile Asn Pro Val Gln Ile Leu Ser Ile Tyr Ser Ala Leu
100 105 110

Glu Asn Asn Gly Asn Ile Asn Ala Pro His Leu Leu Lys Asp Thr Lys
115 120 125

Asn Lys Val Trp Lys Lys Asn Ile Ile Ser Lys Glu Asn Ile Asn Leu
130 135 140

Leu Thr Asp Gly Met Gln Gln Val Val Asn Lys Thr His Lys Glu Asp
145 150 155 160

Ile Tyr Arg Ser Tyr Ala Asn Leu Ile Gly Lys Ser Gly Thr Ala Glu
165 170 175

Leu Lys Met Lys Gln Gly Glu Thr Gly Arg Gln Ile Gly Trp Phe Ile
180 185 190

Ser Tyr Asp Lys Asp Asn Pro Asn Met Met Met Ala Ile Asn Val Lys
195 200 205

Asp Val Gln Asp Lys Gly Met Ala Ser Tyr Asn Ala Lys Ile Ser Gly
210 215 220

Lys Val Tyr Asp Glu Leu Tyr Glu Asn Gly Asn Lys Lys Tyr Asp Ile
225 230 235 240

Asp Glu

<210> SEQ ID NO 7
<211> LENGTH: 2058
<212> TYPE: DNA
<213> ORGANISM: Artificial Sequence
<220> FEATURE:
<223> OTHER INFORMATION: Full MRSA antigen + IgE nucleic acid

<400> SEQUENCE: 7
atggactgga catggattct gttcctggtc gctgctgcta cacgggtgca ttctaaaaag 60

-continued

```
atcaagattg tgcctctgat tctgattgtg gtcgtggtcg gattcggcat ctacttctac    120
gcaagcaagg acaaagagat caacaatact atcgacgcca ttgaagataa gaacttcaaa    180
caggtgtaca aagacagctc ctatatctca aagagcgata atggagaggt cgaaatgaca    240
gagcgcccca tcaaaatcta caactccctg ggcgtgaagg acatcaacat ccaggatagg    300
aaaatcaaga aagtgtctaa gaacaagaaa cgcgtcgatg cccagtacaa gatcaagacc    360
aactatggca atatcgaccg aaacgtgcag ttcaattttg tcaaagagga tggcatgtgg    420
aagctggact gggatcactc tgtgatcatt cctgggatgc agaaggacca gtcaatccat    480
attgagaatc tgaaaagcga acggggcaag atcctggata gaaacaatgt ggagctggcc    540
aacacaggca ctgcttacga aatcgggatt gtgcctaaga atgtcagcaa gaaagactac    600
aaggccatcg ctaaagagct gtccatctct gaagactata tcaagcagca gatggatcag    660
aactgggtgc aggacgatac ctttgtgcca ctgaagacag tcaagaaaat ggacgagtac    720
ctgagcgatt tcgccaagaa atttcacctg accacaaacg agactgaaag taggaattac    780
cccctgggca aggctacctc acatctgctg ggctatgtgg gacctattaa ctccgaggaa    840
ctgaagcaga aagagtacaa ggggtataaa gacgatgccg tgatcggcaa gaaagggctg    900
gagaagctgt acgacaagaa actgcagcac gaagatggat atcgggtgac catcgtcgac    960
gataacagca ataccatcgc acatacactg attgagaaga aaaagaaaga cggcaaagat   1020
atccagctga caattgacgc taaggtgcag aagtctatct acaacaacat gaagaacgat   1080
tatgggagtg gaactgccat ccacccacag accggggaac tgctggctct ggtgagtaca   1140
ccatcatacg acgtgtaccc cttcatgtac ggaatgtcca acgaggaata taacaagctg   1200
actgaggata agaaagaacc tctgctgaat aagtttcaga ttactaccag cccagggtcc   1260
actcagaaaa tcctgaccgc catgattgga ctgaacaata agacactgga cgataagact   1320
tcatacaaaa tcgacggcaa ggggtggcag aaggataaaa gctggggcgg gtacaacgtg   1380
accagatatg aggtggtcaa cggcaatatc gacctgaagc aggccatcga atctagtgat   1440
aacatcttct ttgcaagggt cgccctggag ctgggatcta agaaattcga aaagggcatg   1500
aagaaactgg gagtgggcga ggacatcccc agcgattacc ctttttataa cgctcagatt   1560
tccaacaaga atctggacaa tgagatcctg ctggcagata gtgggtacgg acagggcgaa   1620
atcctgatta acccagtgca gatcctgtct atctacagtg cactggagaa caatgggaac   1680
attaatgccc ctcacctgct gaaggacacc aagaacaaag tgtggaagaa aaatatcatc   1740
agcaaggaga acatcaatct gctgacagac ggcatgcagc aggtggtcaa caagactcat   1800
aaagaagata tctaccgatc ctatgctaat ctgatcggaa agtctggcac cgcagagctg   1860
aagatgaaac aggggaaac aggacggcag atcgggtggt tcattagtta cgacaaggat    1920
aaccctaata tgatgatggc cattaacgtg aaagacgtgc aggataaggg aatggcttca   1980
tataatgcaa agatctcagg aaaagtgtat gacgaactgt atgaaaatgg gaacaaaaag   2040
tatgacattg acgaatga                                                 2058
```

```
<210> SEQ ID NO 8
<211> LENGTH: 685
<212> TYPE: PRT
<213> ORGANISM: Artificial Sequence
<220> FEATURE:
<223> OTHER INFORMATION: Full MRSA antigen + IgE amino acid

<400> SEQUENCE: 8
```

-continued

```
Met Asp Trp Thr Trp Ile Leu Phe Leu Val Ala Ala Ala Thr Arg Val
1               5                   10                  15

His Ser Lys Lys Ile Lys Ile Val Pro Leu Ile Leu Ile Val Val Val
            20                  25                  30

Val Gly Phe Gly Ile Tyr Phe Tyr Ala Ser Lys Asp Lys Glu Ile Asn
        35                  40                  45

Asn Thr Ile Asp Ala Ile Glu Asp Lys Asn Phe Lys Gln Val Tyr Lys
    50                  55                  60

Asp Ser Ser Tyr Ile Ser Lys Ser Asp Asn Gly Glu Val Glu Met Thr
65                  70                  75                  80

Glu Arg Pro Ile Lys Ile Tyr Asn Ser Leu Gly Val Lys Asp Ile Asn
                85                  90                  95

Ile Gln Asp Arg Lys Ile Lys Lys Val Ser Lys Asn Lys Lys Arg Val
            100                 105                 110

Asp Ala Gln Tyr Lys Ile Lys Thr Asn Tyr Gly Asn Ile Asp Arg Asn
        115                 120                 125

Val Gln Phe Asn Phe Val Lys Glu Asp Gly Met Trp Lys Leu Asp Trp
    130                 135                 140

Asp His Ser Val Ile Ile Pro Gly Met Gln Lys Asp Gln Ser Ile His
145                 150                 155                 160

Ile Glu Asn Leu Lys Ser Glu Arg Gly Lys Ile Leu Asp Arg Asn Asn
                165                 170                 175

Val Glu Leu Ala Asn Thr Gly Thr Ala Tyr Glu Ile Gly Ile Val Pro
            180                 185                 190

Lys Asn Val Ser Lys Lys Asp Tyr Lys Ala Ile Ala Lys Glu Leu Ser
        195                 200                 205

Ile Ser Glu Asp Tyr Ile Lys Gln Gln Met Asp Gln Asn Trp Val Gln
    210                 215                 220

Asp Asp Thr Phe Val Pro Leu Lys Thr Val Lys Lys Met Asp Glu Tyr
225                 230                 235                 240

Leu Ser Asp Phe Ala Lys Lys Phe His Leu Thr Thr Asn Glu Thr Glu
                245                 250                 255

Ser Arg Asn Tyr Pro Leu Gly Lys Ala Thr Ser His Leu Leu Gly Tyr
            260                 265                 270

Val Gly Pro Ile Asn Ser Glu Glu Leu Lys Gln Lys Glu Tyr Lys Gly
        275                 280                 285

Tyr Lys Asp Asp Ala Val Ile Gly Lys Lys Gly Leu Glu Lys Leu Tyr
    290                 295                 300

Asp Lys Lys Leu Gln His Glu Asp Gly Tyr Arg Val Thr Ile Val Asp
305                 310                 315                 320

Asp Asn Ser Asn Thr Ile Ala His Thr Leu Ile Glu Lys Lys Lys Lys
                325                 330                 335

Asp Gly Lys Asp Ile Gln Leu Thr Ile Asp Ala Lys Val Gln Lys Ser
            340                 345                 350

Ile Tyr Asn Asn Met Lys Asn Asp Tyr Gly Ser Gly Thr Ala Ile His
        355                 360                 365

Pro Gln Thr Gly Glu Leu Leu Ala Leu Val Ser Thr Pro Ser Tyr Asp
    370                 375                 380

Val Tyr Pro Phe Met Tyr Gly Met Ser Asn Glu Glu Tyr Asn Lys Leu
385                 390                 395                 400

Thr Glu Asp Lys Lys Glu Pro Leu Leu Asn Lys Phe Gln Ile Thr Thr
                405                 410                 415

Ser Pro Gly Ser Thr Gln Lys Ile Leu Thr Ala Met Ile Gly Leu Asn
```

-continued

```
            420                 425                 430

Asn Lys Thr Leu Asp Asp Lys Thr Ser Tyr Lys Ile Asp Gly Lys Gly
        435                 440                 445

Trp Gln Lys Asp Lys Ser Trp Gly Gly Tyr Asn Val Thr Arg Tyr Glu
    450                 455                 460

Val Val Asn Gly Asn Ile Asp Leu Lys Gln Ala Ile Glu Ser Ser Asp
465                 470                 475                 480

Asn Ile Phe Phe Ala Arg Val Ala Leu Glu Leu Gly Ser Lys Lys Phe
                485                 490                 495

Glu Lys Gly Met Lys Lys Leu Gly Val Gly Glu Asp Ile Pro Ser Asp
            500                 505                 510

Tyr Pro Phe Tyr Asn Ala Gln Ile Ser Asn Lys Asn Leu Asp Asn Glu
        515                 520                 525

Ile Leu Leu Ala Asp Ser Gly Tyr Gly Gln Gly Glu Ile Leu Ile Asn
    530                 535                 540

Pro Val Gln Ile Leu Ser Ile Tyr Ser Ala Leu Glu Asn Asn Gly Asn
545                 550                 555                 560

Ile Asn Ala Pro His Leu Leu Lys Asp Thr Lys Asn Lys Val Trp Lys
                565                 570                 575

Lys Asn Ile Ile Ser Lys Glu Asn Ile Asn Leu Leu Thr Asp Gly Met
            580                 585                 590

Gln Gln Val Val Asn Lys Thr His Lys Glu Asp Ile Tyr Arg Ser Tyr
        595                 600                 605

Ala Asn Leu Ile Gly Lys Ser Gly Thr Ala Glu Leu Lys Met Lys Gln
    610                 615                 620

Gly Glu Thr Gly Arg Gln Ile Gly Trp Phe Ile Ser Tyr Asp Lys Asp
625                 630                 635                 640

Asn Pro Asn Met Met Met Ala Ile Asn Val Lys Asp Val Gln Asp Lys
                645                 650                 655

Gly Met Ala Ser Tyr Asn Ala Lys Ile Ser Gly Lys Val Tyr Asp Glu
            660                 665                 670

Leu Tyr Glu Asn Gly Asn Lys Lys Tyr Asp Ile Asp Glu
        675                 680                 685
```

<210> SEQ ID NO 9
<211> LENGTH: 1989
<212> TYPE: DNA
<213> ORGANISM: Artificial Sequence
<220> FEATURE:
<223> OTHER INFORMATION: No Anchor antigen coding sequence nucleic acid

<400> SEQUENCE: 9

```
atggactgga cctggattct gttcctggtc gccgccgcaa cccgcgtgca ttcaagcaag     60

gacaaagaga tcaacaatac tatcgacgcc attgaagata agaacttcaa acaggtgtac    120

aaagacagct cctatatctc aaagagcgat aatggagagg tcgaaatgac agagcgcccc    180

atcaaaatct acaactccct gggcgtgaag gacatcaaca tccaggatag gaaaatcaag    240

aaagtgtcta agaacaagaa acgcgtcgat gcccagtaca agatcaagac caactatggc    300

aatatcgacc gaaacgtgca gttcaatttt gtcaaagagg atggcatgtg gaagctggac    360

tgggatcact ctgtgatcat tcctgggatg cagaaggacc agtcaatcca tattgagaat    420

ctgaaaagcg aacggggcaa gatcctggat agaaacaatg tggagctggc caacacaggc    480

actgcttacg aaatcgggat tgtgcctaag aatgtcagca agaaagacta caaggccatc    540

gctaaagagc tgtccatctc tgaagactat atcaagcagc agatggatca gaactgggtg    600
```

```
caggacgata cctttgtgcc actgaagaca gtcaagaaaa tggacgagta cctgagcgat     660

ttcgccaaga aatttcacct gaccacaaac gagactgaaa gtaggaatta ccccctgggc     720

aaggctacct cacatctgct gggctatgtg ggacctatta actccgagga actgaagcag     780

aaagagtaca aggggtataa agacgatgcc gtgatcggca agaaagggct ggagaagctg     840

tacgacaaga aactgcagca cgaagatgga tatcgggtga ccatcgtcga cgataacagc     900

aataccatcg cacatacact gattgagaag aaaaagaaag acggcaaaga tatccagctg     960

acaattgacg ctaaggtgca gaagtctatc tacaacaaca tgaagaacga ttatgggagt    1020

ggaactgcca tccacccaca gaccggggaa ctgctggctc tggtgagtac accatcatac    1080

gacgtgtacc ccttcatgta cggaatgtcc aacgaggaat ataacaagct gactgaggat    1140

aagaaagaac ctctgctgaa taagtttcag attactacca gcccagggtc cactcagaaa    1200

atcctgaccg ccatgattgg actgaacaat aagacactgg acgataagac ttcatacaaa    1260

atcgacggca aggggtggca gaaggataaa agctggggcg ggtacaacgt gaccagatat    1320

gaggtggtca acggcaatat cgacctgaag caggccatcg aatctagtga taacatcttc    1380

tttgcaaggg tcgccctgga gctgggatct aagaaattcg aaaagggcat gaagaaactg    1440

ggagtgggcg aggacatccc cagcgattac cctttttata acgctcagat ttccaacaag    1500

aatctggaca atgagatcct gctggcagat agtgggtacg gacagggcga aatcctgatt    1560

aacccagtgc agatcctgtc tatctacagt gcactggaga acaatgggaa cattaatgcc    1620

cctcacctgc tgaaggacac caagaacaaa gtgtggaaga aaaatatcat cagcaaggag    1680

aacatcaatc tgctgacaga cggcatgcag caggtggtca acaagactca taaagaagat    1740

atctaccgat cctatgctaa tctgatcgga aagtctggca ccgcagagct gaagatgaaa    1800

caggggggaaa caggacggca gatcgggtgg ttcattagtt acgacaagga taaccctaat    1860

atgatgatgg ccattaacgt gaaagacgtg caggataagg gaatggcttc atataatgca    1920

aagatctcag gaaaagtgta tgacgaactg tatgaaaatg gaaataagaa atatgacatt    1980

gacgaatga                                                            1989
```

<210> SEQ ID NO 10
<211> LENGTH: 662
<212> TYPE: PRT
<213> ORGANISM: Artificial Sequence
<220> FEATURE:
<223> OTHER INFORMATION: No Anchor antigen amino acid sequence

<400> SEQUENCE: 10

```
Met Asp Trp Thr Trp Ile Leu Phe Leu Val Ala Ala Ala Thr Arg Val
1               5                   10                  15

His Ser Ser Lys Asp Lys Glu Ile Asn Asn Thr Ile Asp Ala Ile Glu
            20                  25                  30

Asp Lys Asn Phe Lys Gln Val Tyr Lys Asp Ser Ser Tyr Ile Ser Lys
        35                  40                  45

Ser Asp Asn Gly Glu Val Glu Met Thr Glu Arg Pro Ile Lys Ile Tyr
    50                  55                  60

Asn Ser Leu Gly Val Lys Asp Ile Asn Ile Gln Asp Arg Lys Ile Lys
65                  70                  75                  80

Lys Val Ser Lys Asn Lys Lys Arg Val Asp Ala Gln Tyr Lys Ile Lys
                85                  90                  95

Thr Asn Tyr Gly Asn Ile Asp Arg Asn Val Gln Phe Asn Phe Val Lys
            100                 105                 110
```

-continued

```
Glu Asp Gly Met Trp Lys Leu Asp Trp Asp His Ser Val Ile Ile Pro
        115                 120                 125

Gly Met Gln Lys Asp Gln Ser Ile His Ile Glu Asn Leu Lys Ser Glu
    130                 135                 140

Arg Gly Lys Ile Leu Asp Arg Asn Asn Val Glu Leu Ala Asn Thr Gly
145                 150                 155                 160

Thr Ala Tyr Glu Ile Gly Ile Val Pro Lys Asn Val Ser Lys Lys Asp
                165                 170                 175

Tyr Lys Ala Ile Ala Lys Glu Leu Ser Ile Ser Glu Asp Tyr Ile Lys
            180                 185                 190

Gln Gln Met Asp Gln Asn Trp Val Gln Asp Asp Thr Phe Val Pro Leu
        195                 200                 205

Lys Thr Val Lys Lys Met Asp Glu Tyr Leu Ser Asp Phe Ala Lys Lys
    210                 215                 220

Phe His Leu Thr Thr Asn Glu Thr Glu Ser Arg Asn Tyr Pro Leu Gly
225                 230                 235                 240

Lys Ala Thr Ser His Leu Leu Gly Tyr Val Gly Pro Ile Asn Ser Glu
                245                 250                 255

Glu Leu Lys Gln Lys Glu Tyr Lys Gly Tyr Lys Asp Asp Ala Val Ile
            260                 265                 270

Gly Lys Lys Gly Leu Glu Lys Leu Tyr Asp Lys Lys Leu Gln His Glu
        275                 280                 285

Asp Gly Tyr Arg Val Thr Ile Val Asp Asp Asn Ser Asn Thr Ile Ala
    290                 295                 300

His Thr Leu Ile Glu Lys Lys Lys Lys Asp Gly Lys Asp Ile Gln Leu
305                 310                 315                 320

Thr Ile Asp Ala Lys Val Gln Lys Ser Ile Tyr Asn Asn Met Lys Asn
                325                 330                 335

Asp Tyr Gly Ser Gly Thr Ala Ile His Pro Gln Thr Gly Glu Leu Leu
            340                 345                 350

Ala Leu Val Ser Thr Pro Ser Tyr Asp Val Tyr Pro Phe Met Tyr Gly
        355                 360                 365

Met Ser Asn Glu Glu Tyr Asn Lys Leu Thr Glu Asp Lys Lys Glu Pro
    370                 375                 380

Leu Leu Asn Lys Phe Gln Ile Thr Thr Ser Pro Gly Ser Thr Gln Lys
385                 390                 395                 400

Ile Leu Thr Ala Met Ile Gly Leu Asn Asn Lys Thr Leu Asp Asp Lys
                405                 410                 415

Thr Ser Tyr Lys Ile Asp Gly Lys Gly Trp Gln Lys Asp Lys Ser Trp
            420                 425                 430

Gly Gly Tyr Asn Val Thr Arg Tyr Glu Val Val Asn Gly Asn Ile Asp
        435                 440                 445

Leu Lys Gln Ala Ile Glu Ser Ser Asp Asn Ile Phe Phe Ala Arg Val
    450                 455                 460

Ala Leu Glu Leu Gly Ser Lys Lys Phe Glu Lys Gly Met Lys Lys Leu
465                 470                 475                 480

Gly Val Gly Glu Asp Ile Pro Ser Asp Tyr Pro Phe Tyr Asn Ala Gln
                485                 490                 495

Ile Ser Asn Lys Asn Leu Asp Asn Glu Ile Leu Leu Ala Asp Ser Gly
            500                 505                 510

Tyr Gly Gln Gly Glu Ile Leu Ile Asn Pro Val Gln Ile Leu Ser Ile
        515                 520                 525
```

-continued

```
Tyr Ser Ala Leu Glu Asn Asn Gly Asn Ile Asn Ala Pro His Leu Leu
    530                 535                 540

Lys Asp Thr Lys Asn Lys Val Trp Lys Lys Asn Ile Ile Ser Lys Glu
545                 550                 555                 560

Asn Ile Asn Leu Leu Thr Asp Gly Met Gln Gln Val Val Asn Lys Thr
                565                 570                 575

His Lys Glu Asp Ile Tyr Arg Ser Tyr Ala Asn Leu Ile Gly Lys Ser
            580                 585                 590

Gly Thr Ala Glu Leu Lys Met Lys Gln Gly Glu Thr Gly Arg Gln Ile
        595                 600                 605

Gly Trp Phe Ile Ser Tyr Asp Lys Asp Asn Pro Asn Met Met Met Ala
    610                 615                 620

Ile Asn Val Lys Asp Val Gln Asp Lys Gly Met Ala Ser Tyr Asn Ala
625                 630                 635                 640

Lys Ile Ser Gly Lys Val Tyr Asp Glu Leu Tyr Glu Asn Gly Asn Lys
                645                 650                 655

Lys Tyr Asp Ile Asp Glu
            660


<210> SEQ ID NO 11
<211> LENGTH: 783
<212> TYPE: DNA
<213> ORGANISM: Artificial Sequence
<220> FEATURE:
<223> OTHER INFORMATION: Short PBP2a catalytic + IgE nucleic acid

<400> SEQUENCE: 11

atggactgga catggattct gttcctggtc gctgctgcta cacgggtgca ttctatcgac      60

ggcaaggggt ggcagaagga taaaagctgg ggcgggtaca acgtgaccag atatgaggtg     120

gtcaacggca atatcgacct gaagcaggcc atcgaatcta gtgataacat cttctttgca     180

agggtcgccc tggagctggg atctaagaaa ttcgaaaagg gcatgaagaa actgggagtg     240

ggcgaggaca tccccagcga ttaccctttt tataacgctc agatttccaa caagaatctg     300

gacaatgaga tcctgctggc agatagtggg tacggacagg gcgaaatcct gattaaccca     360

gtgcagatcc tgtctatcta cagtgcactg gagaacaatg ggaacattaa tgcccctcac     420

ctgctgaagg acaccaagaa caaagtgtgg aagaaaaata tcatcagcaa ggagaacatc     480

aatctgctga cagacggcat gcagcaggtg gtcaacaaga ctcataaaga agatatctac     540

cgatcctatg ctaatctgat cggaaagtct ggcaccgcag agctgaagat gaaacagggg     600

gaaacaggac ggcagatcgg gtggttcatt agttacgaca aggataaccc taatatgatg     660

atggccatta acgtgaaaga cgtgcaggat aagggaatgg cttcatataa tgcaaagatc     720

tcaggaaaag tgtatgacga actgtatgaa aatgggaaca aaaagtatga cattgacgaa     780

tga                                                                   783


<210> SEQ ID NO 12
<211> LENGTH: 260
<212> TYPE: PRT
<213> ORGANISM: Artificial Sequence
<220> FEATURE:
<223> OTHER INFORMATION: Short PBP2a catalytic + IgE amino acid

<400> SEQUENCE: 12

Met Asp Trp Thr Trp Ile Leu Phe Leu Val Ala Ala Ala Thr Arg Val
1               5                   10                  15

His Ser Ile Asp Gly Lys Gly Trp Gln Lys Asp Lys Ser Trp Gly Gly
```

-continued

```
            20                  25                  30

Tyr Asn Val Thr Arg Tyr Glu Val Val Asn Gly Asn Ile Asp Leu Lys
        35                  40                  45

Gln Ala Ile Glu Ser Ser Asp Asn Ile Phe Phe Ala Arg Val Ala Leu
    50                  55                  60

Glu Leu Gly Ser Lys Lys Phe Glu Lys Gly Met Lys Lys Leu Gly Val
65                  70                  75                  80

Gly Glu Asp Ile Pro Ser Asp Tyr Pro Phe Tyr Asn Ala Gln Ile Ser
                85                  90                  95

Asn Lys Asn Leu Asp Asn Glu Ile Leu Leu Ala Asp Ser Gly Tyr Gly
            100                 105                 110

Gln Gly Glu Ile Leu Ile Asn Pro Val Gln Ile Leu Ser Ile Tyr Ser
        115                 120                 125

Ala Leu Glu Asn Asn Gly Asn Ile Asn Ala Pro His Leu Leu Lys Asp
    130                 135                 140

Thr Lys Asn Lys Val Trp Lys Lys Asn Ile Ile Ser Lys Glu Asn Ile
145                 150                 155                 160

Asn Leu Leu Thr Asp Gly Met Gln Gln Val Val Asn Lys Thr His Lys
                165                 170                 175

Glu Asp Ile Tyr Arg Ser Tyr Ala Asn Leu Ile Gly Lys Ser Gly Thr
            180                 185                 190

Ala Glu Leu Lys Met Lys Gln Gly Glu Thr Gly Arg Gln Ile Gly Trp
        195                 200                 205

Phe Ile Ser Tyr Asp Lys Asp Asn Pro Asn Met Met Met Ala Ile Asn
    210                 215                 220

Val Lys Asp Val Gln Asp Lys Gly Met Ala Ser Tyr Asn Ala Lys Ile
225                 230                 235                 240

Ser Gly Lys Val Tyr Asp Glu Leu Tyr Glu Asn Gly Asn Lys Lys Tyr
                245                 250                 255

Asp Ile Asp Glu
            260


<210> SEQ ID NO 13
<211> LENGTH: 17
<212> TYPE: PRT
<213> ORGANISM: Artificial Sequence
<220> FEATURE:
<223> OTHER INFORMATION: IgE leader

<400> SEQUENCE: 13

Met Asp Trp Thr Trp Ile Leu Phe Leu Val Ala Ala Ala Thr Arg Val
1               5                   10                  15

His
```